(12) United States Patent
Gitlin et al.

(10) Patent No.: US 9,451,890 B2
(45) Date of Patent: Sep. 27, 2016

(54) INTEGRATED VECTORCARDIOGRAM SYSTEM AND METHOD OF USE

(71) Applicants: Richard Dennis Gitlin, Tampa, FL (US); Gabriel Eduardo Arrobo, Emeryville, CA (US); Peter Jeffrey Fabri, Tampa, FL (US); Thomas Petter Ketterl, Tampa, FL (US); Calvin Perumalla, Tampa, FL (US)

(72) Inventors: Richard Dennis Gitlin, Tampa, FL (US); Gabriel Eduardo Arrobo, Emeryville, CA (US); Peter Jeffrey Fabri, Tampa, FL (US); Thomas Petter Ketterl, Tampa, FL (US); Calvin Perumalla, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/801,514

(22) Filed: Jul. 16, 2015

(65) Prior Publication Data
US 2016/0015286 A1 Jan. 21, 2016

Related U.S. Application Data

(60) Provisional application No. 62/025,308, filed on Jul. 16, 2014.

(51) Int. Cl.
*A61B 5/04* (2006.01)
*A61B 5/0402* (2006.01)
(Continued)

(52) U.S. Cl.
CPC ......... *A61B 5/04011* (2013.01); *A61B 5/0006* (2013.01); *A61B 5/04028* (2013.01); *A61B 5/742* (2013.01); *A61N 1/36514* (2013.01); *A61N 1/37235* (2013.01);
(Continued)

(58) Field of Classification Search
CPC ................. A61N 1/37235; A61N 1/36514; A61N 1/3962; A61N 1/37288; A61N 1/3756; A61B 5/742; A61B 5/04011; A61B 5/04028; A61B 5/006
See application file for complete search history.

(56) References Cited

U.S. PATENT DOCUMENTS 6,631,290 B1 10/2003 Guck et al.
7,647,093 B2 * 1/2010 Bojovic ............... A61B 5/0006
600/509
(Continued)

FOREIGN PATENT DOCUMENTS

CN 2034353 U 3/1989

OTHER PUBLICATIONS

Translation of foreign patent CN2034353, titled Multifuctional Biologic Amplfirer Interfaced with Computer, with a publication date of Mar. 15, 1989; Applicant: NO 180 Hospital PLA.
(Continued)

*Primary Examiner* — Mallika D Fairchild
(74) *Attorney, Agent, or Firm* — Molly L. Sauter; Nilay J. Choksi; Smith & Hopen, P.A.

(57) ABSTRACT

An integrated vectorcardiogram (VCG) device having 3 pairs of electrodes placed in three orthogonal directions with the capability to continuously measure the electrical activity of the heart. All of the electrode pairs may be contained within a single miniaturized housing thereby eliminating the need for cumbersome wires required with current 12-lead ECG systems, while providing the same amount and quality of information as the 12-lead ECG system. The integrated VCG device also includes a communications function to allow the data collected by the electrodes to be transmitted wirelessly to a remote device, such as a pacemaker, to control its function or to a remote monitoring station for continuous real-time patient monitoring.

27 Claims, 19 Drawing Sheets

(51) Int. Cl.
*A61B 5/00* (2006.01)
*A61N 1/365* (2006.01)
*A61N 1/372* (2006.01)
*A61N 1/375* (2006.01)
*A61N 1/39* (2006.01)

(52) U.S. Cl.
CPC ..... *A61B 2560/0468* (2013.01); *A61N 1/3756* (2013.01); *A61N 1/37288* (2013.01); *A61N 1/3962* (2013.01)

(56) References Cited

U.S. PATENT DOCUMENTS

| | | |
|---|---|---|
| 2001/0034487 A1 | 10/2001 | Cao et al. |
| 2003/0083587 A1 | 5/2003 | Ferek-Petric |
| 2014/0107501 A1 | 4/2014 | Komanduri et al. |

OTHER PUBLICATIONS

International Search Report and Written Opinion for PCT/US15/40780 (filing date: Jul. 16, 2015) with a mailing date of Oct. 23, 2015; Applicant: University of South Flordia.

Gupta. Respiration Rate Measurement Based on Impedance Pneumography. Texas Instruments Application Report. 2011. SBAA181: 1-11.

Malmivuo and Plonsey. Bioelectromagnetism: Principles and Applications of Bioelectric and Biomagnetic Fields. Oxford University Press. 1995.

Frank. An Accurate, Clinically Practical System for Spatial Vectorcardiography. Circulation. 1956. vol. 13: 737-749.

Koivumaki et al., Bioimpedance-based measurement method for simultaneous acquisition of respiratory and cardiac gating signals. Physiol. Meas. 2012. vol. 33: 1323-1334.

Kachenoura et al., Using Intracardiac Vectorcardiographic Loop for Surface ECG Synthesis. EURASIP Journal on Advances in Signal Processing. 2008. Article ID 410630: 1-8.

Li et al., Computer interpretation of the 12-lead electrocardiogram, the Frank-lead vectorcardiogram and the reconstructed vectorcardiogram. Computers in Cardiology. 1994: 321-324.

Huang et al., A vectorcardiogram based classification system for the detection of Myocardial infarction. Conf Proc IEEE Eng Med Biol Soc (EMBS). 2011: 973-976.

Burch. The history of vectorcardiography. Med Hist Suppl. 1985. vol. 5: 103-131.

Mann. A method of analyzing the electrocardiogram. Arch Intern Med. 1920. vol. 25: 283-294.

Yang et al., Spatiotemporal representation of cardiac vectorcardiogram (VCG) signals. BioMed Eng OnLine. 2012. vol. 11: 1-15.

Liu et al., Multiscale Adaptive Basis Function Modeling of Spatiotemporal Vectorcardiogram Signals. IEEE Journal of Biomedical and Health Informatics. 2013. vol. 17 (No. 2): 484-492.

Schreurs et al., the spatial QRS-T angle in the Frank vectorcardiogram: accuracy of estimates derived from the 12-lead electrocardiogram. Journal of Electrocardiology. 2010. vol. 43: 294-301.

Schau et al., Baseline vectorcardiography as a predictor of invasively determined acute hemodynamic response to cardiac resynchronization therapy. Clin Res Cardiol. 2013. vol. 102: 129-138.

Ghista et al., Frontal Plane Vectorcardiograms: Theory and Graphics Visualization of Cardiac Health Status. J Med Syst. 2010. vol. 34: 445-458.

Loring et al., Modeling vectorcardiograms based on left ventricle papillary muscle position. Journal of Electrocardiology. 2011. vol. 44: 584-589.

Vullings et al., Bayesian Approach to Patient-Tailored Vectorcardiography. IEEE Transactions on Biomedical Engineering. 2010. vol. 57 (No. 3): 586-595.

Schreck et al., Derivation of the 12-lead electrocardiogram and 3-lead vectorcardiogram. The American Journal of Emergency Medicine. 2013. vol. 31: 1183-1190.

Dawson et al., Linear affine transformations between 3-lead (Frank XYZ leads) vectorcardiogram and 12-lead electrocardiogram signals. Journal of Electrocardiology. 2009. vol. 42: 622-630.

\* cited by examiner

INTEGRATED VECTORCARDIOGRAM SYSTEM AND METHOD OF USE

CROSS-REFERENCE TO RELATED APPLICATION

This patent application claims priority to U.S. Provisional Patent Application No. 62/025,308, entitled, "Vectorcardiogram (VCG) System and Method," filed on Jul. 16, 2014, the contents of which are hereby incorporated by reference.

FIELD OF THE INVENTION

Embodiments of the invention relate, generally, to cardiac monitoring. Certain embodiments of the present invention relate more specifically to an integrated vectorcardiogram device and method for advanced, portable, long term and/or continuous monitoring of a patient's electrical heart activity.

BACKGROUND OF THE INVENTION

Vectorcardiography is a method to calculate, for each time instant, the magnitude and direction of electrical forces generated by the heart, commonly referred to as the resultant cardiac, or heart, vector, as sensed by electrical leads mounted on the skin surface of a patient. A vectorcardiogram (VCG) presents a compact three-dimensional (3D) view of the depolarization, or depolarization cycle, of the heart. The resultant cardiac vector may be viewed as three (3) projections of the polarization event of the heart on the coronal (frontal), transverse (horizontal) and sagittal (vertical) plane or directly as a vector. Vectorcardiography is presently used mostly for didactic purposes to teach students of biomedical sciences, physiological aspects of electrocardiography. The 3-lead VCG and the 12-lead ECG (electrocardiogram) present the same comprehensive diagnostic information concerning the electrical activity of the heart, albeit in different formats.

To the trained clinician, an ECG conveys a large amount of information about the structure of the heart and the function of its electrical conduction system. Among other things, an ECG can be used to measure the rate and rhythm of heartbeats, the size and position of the heart chambers, the presence of any damage to the heart's muscle cells or conduction system, the effects of cardiac drugs and the function of implanted pacemakers.

Current ambulatory monitoring systems have limited monitoring capability\ and do not have the diagnostic-quality monitoring fidelity of the 12-lead ECG, sometimes referred to as the "gold standard" for electrocardiography in the medical industry. Additionally, 12-lead ECG machines contain wires that connect the leads to the ECG machine, thereby restricting patient mobility and rendering the ECG machines nearly impossible to be used by the patient outside the clinic or hospital.

Accordingly, what is needed in the art is an improved integrated vectorcardiogram system and methodology that facilitates continuous, real-time, comprehensive, unobtrusive, remote, diagnostic-quality cardiac monitoring. However, in view of the art considered as a whole at the time the present invention was made, it was not obvious to those of ordinary skill in the field of this invention how the shortcomings of the prior art could be overcome.

SUMMARY OF THE INVENTION

According to certain embodiments of the present invention, an integrated vectorcardiogram system may be provided, where either all or substantially all of the leads (e.g., all but a single lead externally connected to the integrated VCG device) are completely contained within the integrated vectorcardiogram system, thereby at least substantially, if not completely, eliminating external wires.

In one embodiment, an integrated vectorcardiogram (VCG) device for measuring cardiac electrical activity of a patient is provided. The integrated VCG device includes a pair of substantially orthogonal X-axis electrodes, a pair of substantially orthogonal Y-axis electrodes and a first Z-axis electrode of a pair of substantially orthogonal Z-axis electrodes, the electrodes contained within a housing adapted to be in contact with a patient in a vectorcardiogram measurement position to sense cardiac electrical signals of the patient. The integrated VCG device further includes, analog processing circuitry contained within the housing, the analog processing circuitry coupled to receive the cardiac electrical signals sensed by the pair of substantially orthogonal X-axis electrodes, the pair of substantially orthogonal Y-axis electrodes and the first Z-axis electrode of the pair of substantially orthogonal Z-axis electrodes. The integrated VCG device additionally includes, a second Z-axis electrode of the pair of substantially orthogonal Z-axis electrodes adapted to be in contact with the patient in a vectorcardiogram measurement position and coupled to the analog processing circuitry, the second Z-axis electrode to sense cardiac electrical signals of the patient and the analog processing circuitry to receive the cardiac electrical signals from the second Z-axis electrode. The VCG device further includes, an analog-to-digital converter contained within the housing, the analog-to-digital converter coupled to the analog processing circuitry to convert the cardiac electrical signals to digital vectorcardiogram data, a digital signal processor contained within the housing, the digital signal processor coupled to receive the digital vectorcardiogram data from the analog-to-digital converter to generate processed digital vectorcardiogram data and telemetry circuitry contained within the housing, the telemetry circuitry coupled to receive the processed digital vectorcardiogram data from the digital signal processor and to transmit the data to a remote device.

In one embodiment of the integrated VCG device, the second Z-axis electrode of the pair of substantially orthogonal Z-axis electrodes may be contained within the housing. In an additional embodiment, the second Z-axis electrode of the pair of substantially orthogonal Z-axis electrodes may be coupled to the analog processing circuitry by an external lead and adapted to contact the patient in a measurement position.

In an additional embodiment, a method for measuring cardiac electrical activity of a patient includes, positioning a vectorcardiogram device in a measurement position relative to a patient, wherein the vectorcardiogram device includes a pair of substantially orthogonal X-axis electrodes, a pair of substantially orthogonal Y-axis electrodes and a first Z-axis electrode of a pair of substantially orthogonal Z-axis electrodes, the electrodes contained within a housing adapted to be in contact with a patient in a vectorcardiogram measurement position to sense cardiac electrical signals of the patient. The integrated VCG device further includes, analog processing circuitry contained within the housing, the analog processing circuitry coupled to receive the cardiac electrical signals sensed by the pair of substantially orthogonal X-axis electrodes, the pair of substantially orthogonal Y-axis electrodes and the first Z-axis electrode of the pair of substantially orthogonal Z-axis electrodes. The integrated VCG device additionally includes, a second Z-axis electrode of the pair of substantially orthogonal Z-axis electrodes adapted to be in contact with the patient in a vectorcardiogram measurement position and coupled to the analog processing circuitry, the second Z-axis electrode to sense cardiac electrical signals of the patient and the analog processing circuitry to receive the cardiac electrical signals from the second Z-axis electrode. The integrated VCG device further includes, an analog-to-digital converter contained within the housing, the analog-to-digital converter coupled to the analog processing circuitry to convert the cardiac electrical signals to digital vectorcardiogram data, a digital signal processor contained within the housing, the digital signal processor coupled to receive the digital vectorcardiogram data from the analog-to-digital converter to generate processed digital vectorcardiogram data and telemetry circuitry contained within the housing, the telemetry circuitry coupled to the receive the processed digital vectorcardiogram data from the digital signal processor and to transmit the data to a remote device.

In the method of the present invention, the second Z-axis electrode may be internal or external to the housing of the integrated VCG device. Additionally, the measurement position of the integrated VCG device may be external to the patient, wherein the device is in contact with the skin of the patient, or alternatively the measurement position of the integrated VCG device may be internal to the patient, wherein the device is implanted within the body of the patient.

In various embodiments, the present invention provides an improved integrated vectorcardiogram system and methodology that facilitates continuous, real-time, comprehensive, unobtrusive, remote, diagnostic-quality cardiac monitoring.

BRIEF DESCRIPTION OF THE DRAWINGS

For a fuller understanding of the invention, reference should be made to the following detailed description (noted that if "ground" is not mentioned in the measurements figures, there was no ground reference used when taking those measurements), taken in connection with the accompanying drawings, in which.

DETAILED DESCRIPTION OF THE INVENTION

Figure 1:
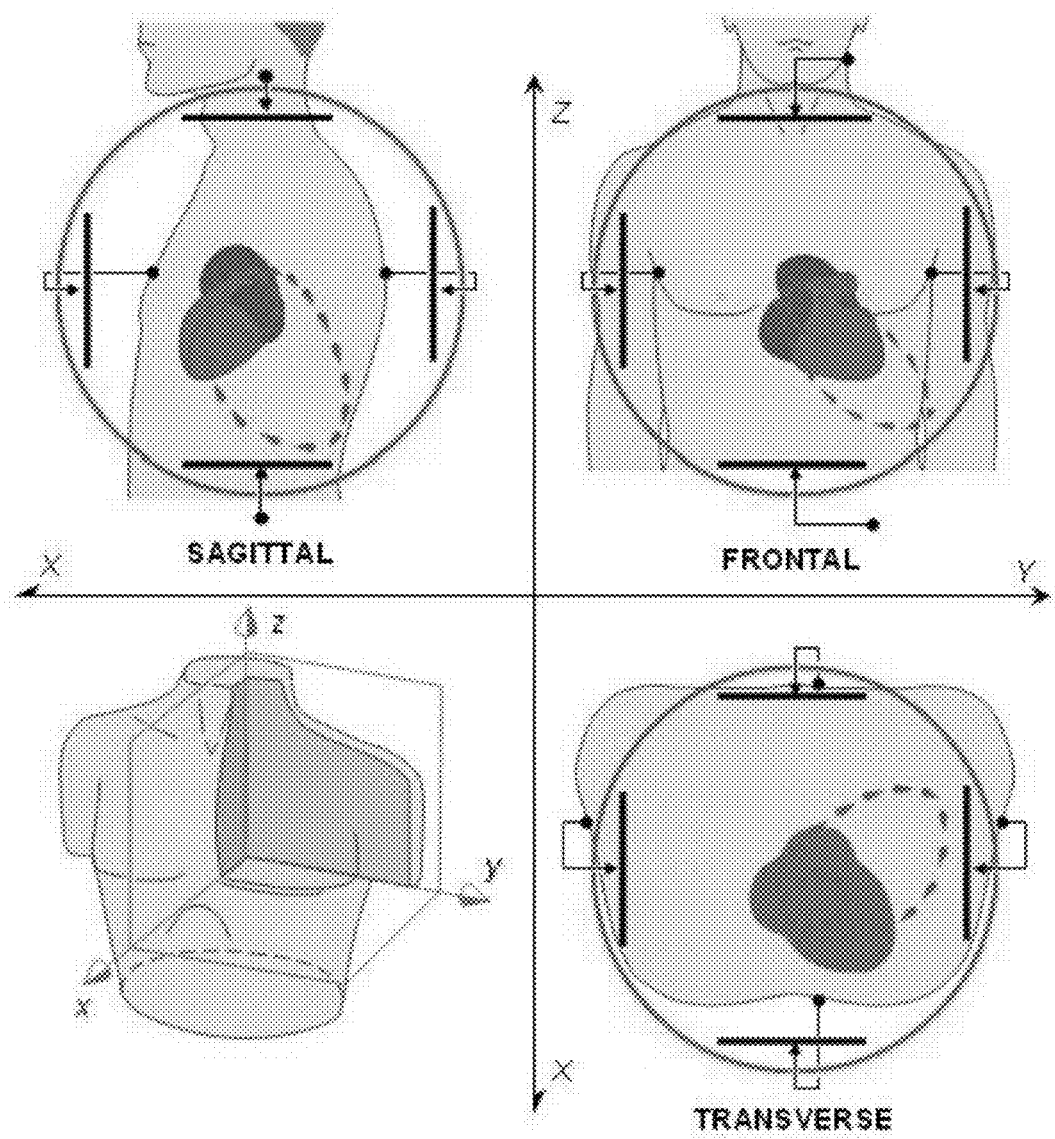
FIG. 1 illustrates the VCG in three Cartesian planes with VCG loops indicated, in accordance with an embodiment of the present invention.

In the following detailed description of the invention, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

Generally, the integrated vectorcardiogram methodology is discussed herein to enable comprehensive, continuous, real-time monitoring of the cardiac electrical activity of a patient utilizing a small form-factor device that can be worn on the body of the patient. The principal advantage of the integrated vectorcardiogram is that it provides the same information as the 12-lead ECG but with fewer leads. This is achieved by manipulating the cardiac vector to yield a conventional ECG signal.

In one embodiment, the invention comprises a system and method based on a vectorcardiogram that can continuously monitor, in three dimensions, the electrical activity of the heart with a miniaturized, portable device that enables secure continuous recording of an individual's heart activity. The integrated vectorcardiogram described herein provides the same amount of information as the 12-lead ECG (which is known as the "gold standard" in the field of cardiology), but requires less data (typically only ¼ of the data as the ECG) to be transmitted. For every time sample, a three-element vector, comprised of the X, Y and Z voltage amplitudes, is transmitted. The very small integrated vectorcardiogram device of the present invention is ideally similar in size to a small adhesive bandage, although other sizes are contemplated, which can be placed on-body or can be implanted in the human body. The invention provides long term and continuous remote, wired or wireless, monitoring of a patient's electrical heart activity. The present invention provides a small, portable integrated vectorcardiogram device that can be worn on-body or implanted within a patient, enabling comprehensive and continuous data collection having a quality at least equal to that available from a 12-lead ECG without requiring wires associated with the current 12-lead ECG machines.

In one embodiment, the integrated vectorcardiogram of the present invention provides a cost effective, compact, portable and wirelessly communicating VCG-based device. Through this inventive technology, continuous real-time remote telemonitoring of a patient's heart activity becomes possible. The Holter monitor system, which is currently the standard for ambulatory monitoring of the electrical activity of the heart, is limited in the sense that it can sense only 1-2 dimensions of the heart's electrical activity with 1-3 leads, and is obtrusive due to electrical wires crowding the chest area. Moreover, the Holter monitor can be used for only a limited period of time. The Holter monitor system can be replaced by the integrated VCG system of the present invention for improved cardiac monitoring. Moreover, the integrated VCG of the present invention can reduce the complexity and the cost of intensive care unit (ICU) cardiac monitoring. In addition, physicians can potentially send patients home earlier because the doctors can have continuous remote monitoring of the patients, thereby reducing the overall medical expenses.

Furthermore, continuous remote monitoring of a patient may assist in the prediction of a cardiac event, which may allow physicians to provide preventative health care for the patient, allowing improved patient care and reduced overall medical costs. Research shows that predictive pre-cursor's can be found in the 12-lead ECG in the case of certain heart-related abnormalities. For example, life threatening coronary morbidity and mortality was linked to non-specific ST-T wave changes in an ECG. It was concluded that patients who develop non-specific ST-T wave changes without explanation require rigorous preventative management against coronary heart disease.

FIG. 1 illustrates a view of the VCG signal from three Cartesian planes (X-Y, Y-Z and X-Z). The integrated VCG uses three orthogonal systems of leads to obtain the 3D electrical representation of the heart. The integrated VCG and ECG are both reflections of the electrical cardiac activity of the heart, however, they differ in the recording methodology employed. The quality and the quantity of information in the integrated VCG is at least as comprehensive as the 12-lead ECG and may contain more information that is useful in certain circumstances.

Figure 2:
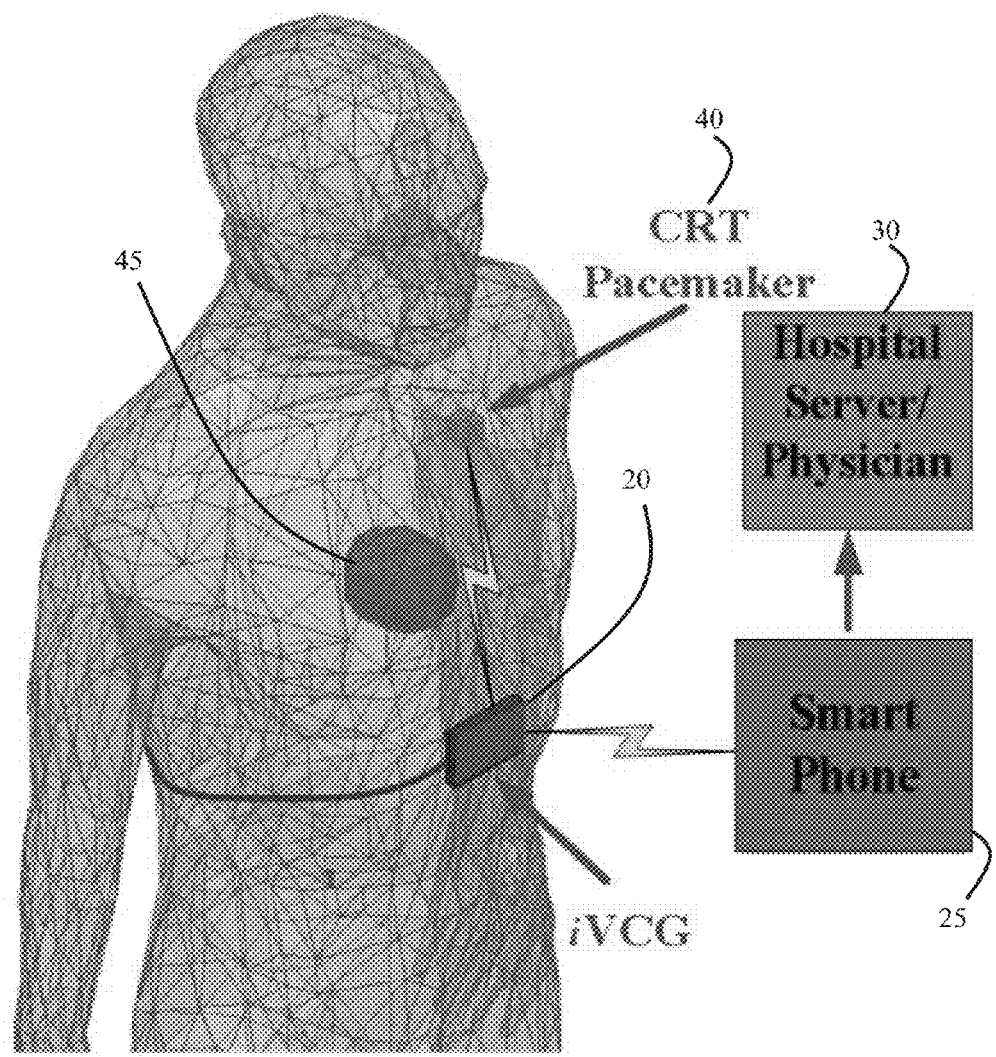
FIG. 2 is illustration of the integrated vectorcardiogram system in accordance with an embodiment of the present invention.

In particular, from FIG. 2, the direction of the cardiac, or heart, vector can be computed from the VCG loops (dashed green curves in FIG. 2). Each VCG loop is a projection of the cardiac vector on the three Cartesian planes.

In accordance with an embodiment of the present invention, an integrated vectorcardiogram device, having a small form factor, is presented herein, wherein the integrated VCG device may be part of an integrated vectorcardiogram system. The integrated VCG device of the present invention has a very small form factor, such that it can be an ambulatory device and can continuously monitor the electrical activity of the heart of a patient in three dimensions.

The integrated VCG device of the present invention contains three pairs of orthogonal leads that are integrated into a small, wearable, device that is designed to be unobtrusive to daily patient activity. Due to the small size of the device, a greatly reduced inter-electrode distance (as compared to the classic VCG system) is required. In the development of the integrated VCG device, the main challenge is to construct a small device, wherein the pairs of electrodes used to capture the electrical activity of the heart in the X, Y and Z dimensions are separated by small inter-electrode distances.

The miniaturized integrated VCG device of the present invention may also incorporate artificial intelligence (machine learning) technology, security and device authentication, and wireless communication capabilities. The integrated vectorcardiogram system may be comprised of a miniaturized wireless integrated VCG device 20, a mobile data system 25 such as, but not limited to, a smart phone and an associated server 30, as shown with reference to FIG. 2. FIG. 2 also illustrates an optional Pacemaker 40 (Cardiac Resynchronization Therapy Device/Implantable Cardioverter Defibrillator) that may be a part of the integrated vectorcardiogram system, which can be controlled by the integrated vectorcardiogram device to regulate the signals to the patient's heart 45.

The integrated vectorcardiogram system enables continuous, comprehensive, long-term, information collection from an outpatient, or in an in-hospital patient, that is identical in content to the data available from the office-based 12-lead ECG. This capability has never been available before.

In one embodiment, the integrated vectorcardiogram device of the present invention is designed to be positioned on the body of a patient, wherein the electrodes are integrated into the housing of the device, or are alternatively adhered to the outer surface of the housing, and are positioned to be in contact with the skin surface of the patient to collect the cardiac electrical signals of the patient's heart. In order to integrate the electrodes within the housing of the device, a minimum allowable distance between the electrodes needs to be determined. To determine the minimum allowable distance between the electrodes, two pairs of electrodes may be placed on the body of the patient, wherein one pair of electrodes is positioned in the X-axis and another pair of electrodes is positioned in the Y-axis, at various distances. In this embodiment, for the Z-axis, one Z-axis electrode may be placed on the chest of the patient and the other Z-axis electrode may be placed on the back of the patient. It was determined that positioning electrodes along all three axes, centered on the heart and two inches above the xiphoid allows for optimization of lead placements for orthogonality and maximum signal fidelity.

As the distance between the leads in the X and Y axes is decreased, the amplitude and wave shape of the signals will, at some point, suffer loss of amplitude and become distorted, as a result of a loss of orthogonality. As such, the 3-lead VCG signal will be degraded relative to that of a 12-lead ECG.

Figure 3A:
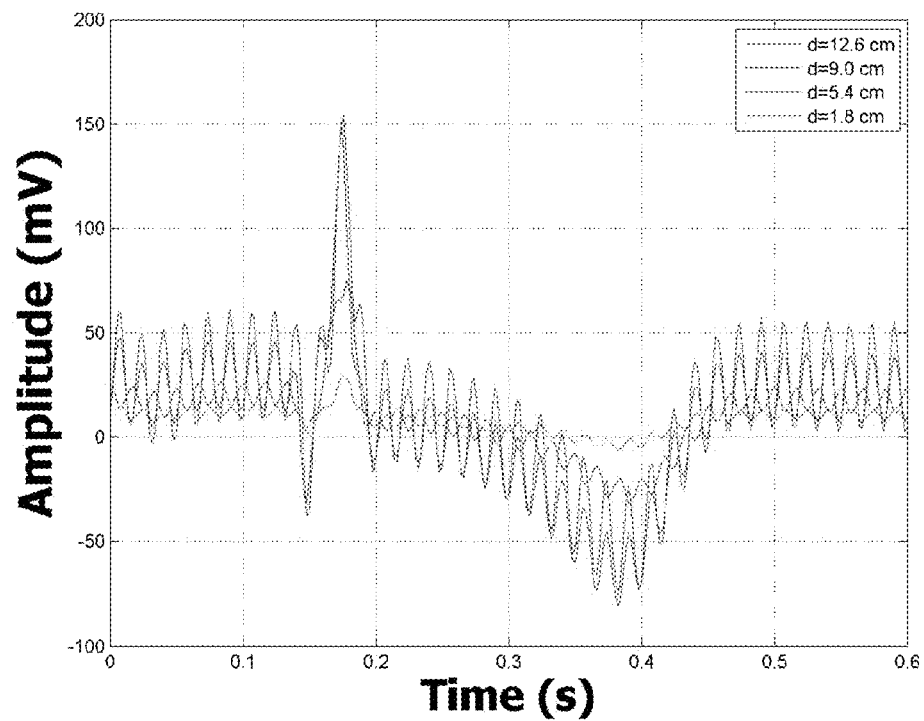
FIG. 3A shows the measured signals for different distances for a pair of electrodes in the X-axis, in accordance with an embodiment of the present invention.
Figure 3B:
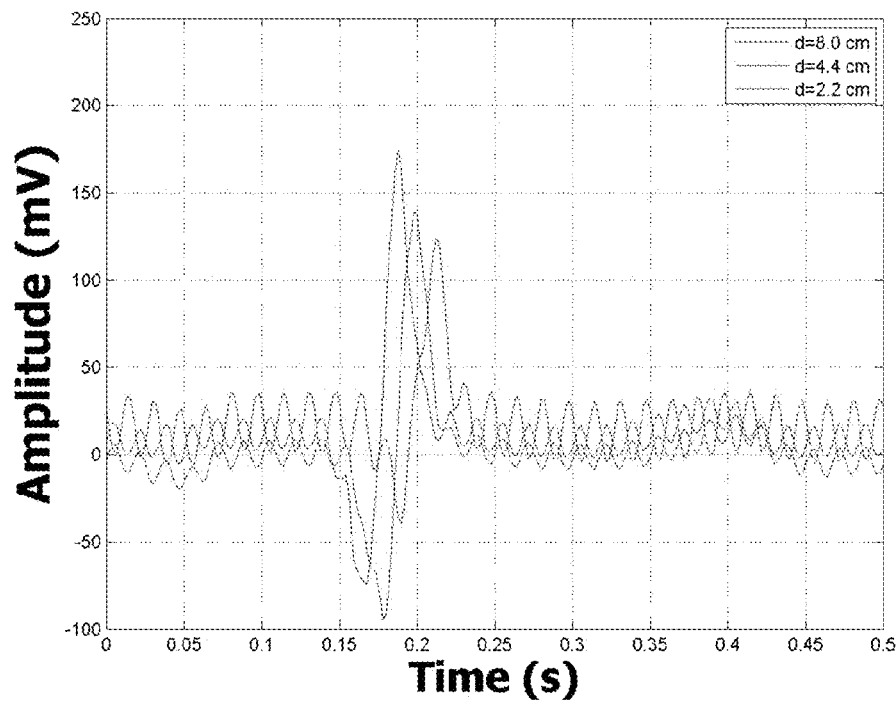
FIG. 3B shows the measured signals for different distances for a pair of electrodes in the X-axis (with a shorter time interval shown for clarity), in accordance with an embodiment of the present invention.
Figure 4:
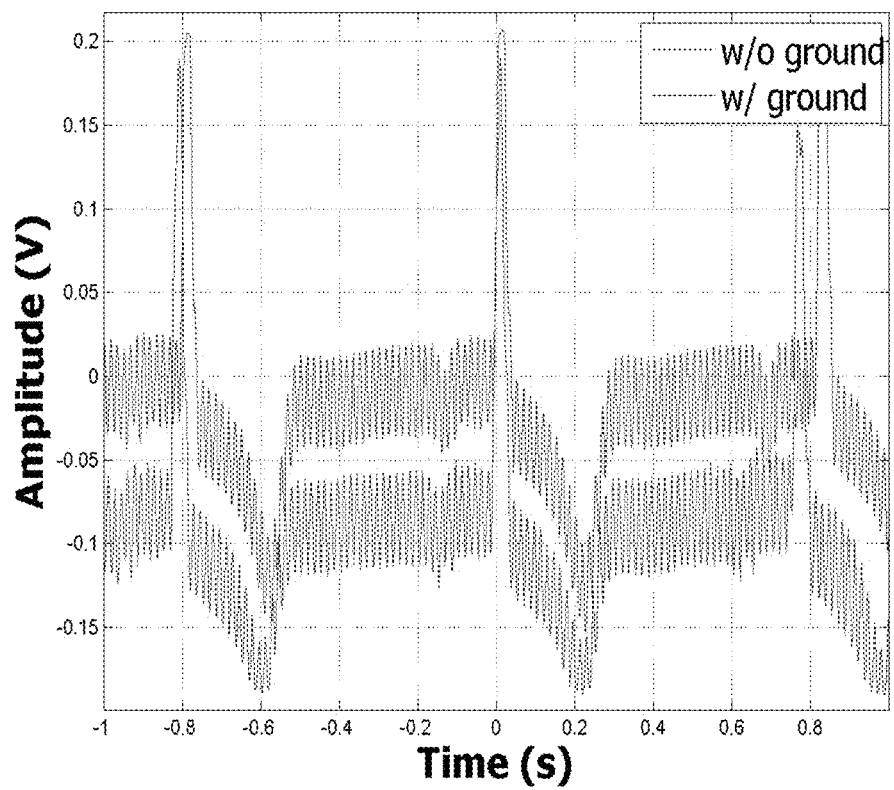
FIG. 4 shows the measured signals between a pair of electrodes in the Z-axis, in accordance with an embodiment of the present invention.

With reference to FIG. 3A and FIG. 3B, electrical activity of the heart for different distances between the electrodes was measured and data was obtained for distances between about 12.6 cm and about 1.8 cm for electrode leads in the X-axes and for distances between about 8.0 cm and about 2.2 cm for electrode leads in the Y-axes. As illustrated, the measured signals suffer loss of amplitude and become distorted as the distance between the electrodes is decreased. FIG. 4 illustrates the signal data obtained in the Z-axis, wherein a first Z-axis electrode was placed on the chest (Z+), and the other electrode was place on the back (Z−) and measurements were taken with and without a ground lead. The information provide in FIG. 3A, FIG. 3B and FIG. 4 is useful to determine the minimum distance required between the electrodes pairs to provide a satisfactory and accurate diagnostic VCG signal. The effect of a ground lead in the X-axis and Y-axis electrodes may also be considered by incorporating a ground lead into the measurements.

As can be seen in FIG. 3A, FIG. 3B and FIG. 4, the closer the distance between the leads, the smaller the amplitude of the signal and the smaller the signal-to-noise ratio, since the noise power remains the same. These signals illustrated in FIG. 3A, FIG. 3B and FIG. 4 are presented in scalar form and will be subsequently transmitted in vector form [X, Y, Z].

The results provided in FIG. 3A, FIG. 3B and FIG. 4 show that an acceptable 3-lead VCG signal can be obtained from three pairs of orthogonal electrodes that are separated by a minimum distance. Incorporating signal processing that allows the electrodes to be separated by a minimum distance provides for an integrated VCG device having a compact form factor that can be used to collect the cardiac electrical signals of a patient. As shown with reference to FIG. 5A, in one embodiment of the present invention, the VCG device 140 comprises a pair of substantially orthogonal X-axis electrodes 100, 105 and a pair of substantially orthogonal Y-axis electrodes 110, 115 contained within a housing 130 or positioned on a substantially planar back surface of the housing 130. In this embodiment, a first Z-axis electrode 120 is contained within the housing 130 and a second Z-axis electrode 125 is connected to the device 140 by a lead. In operation, the integrated VCG device 140 is placed in contact with the chest of the patient at a proper measurement position such that the X-axis electrodes 100, 105, the Y-axis electrodes 110, 115 and the first Z-axis electrode 120 are in contact with the skin of the patient. The second Z-axis electrode 125 is then placed on the back of the patient to form a pair of Z-axis orthogonal leads. The placement of the electrodes in contact with the skin of the patient and in an appropriate measurement positon on the chest of the patient is effective in collecting the cardiac electrical signals of the patient. The housing 130 may further include a display 135 on a substantially planar front surface of the device 130.

Figure 5A:
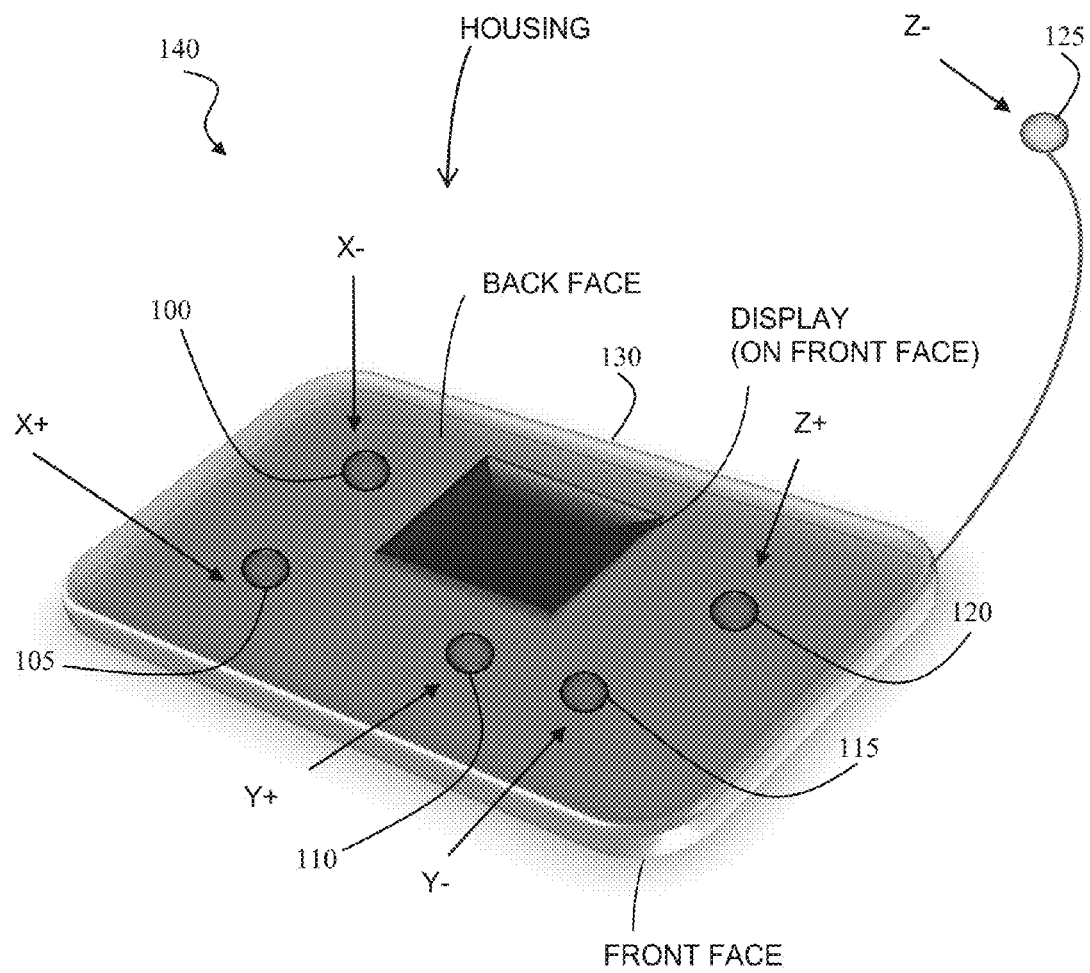
FIG. 5A is perspective view of a single lead external integrated VCG showing the front and back faces of the device, in accordance with an embodiment of the present invention.
Figure 5B:
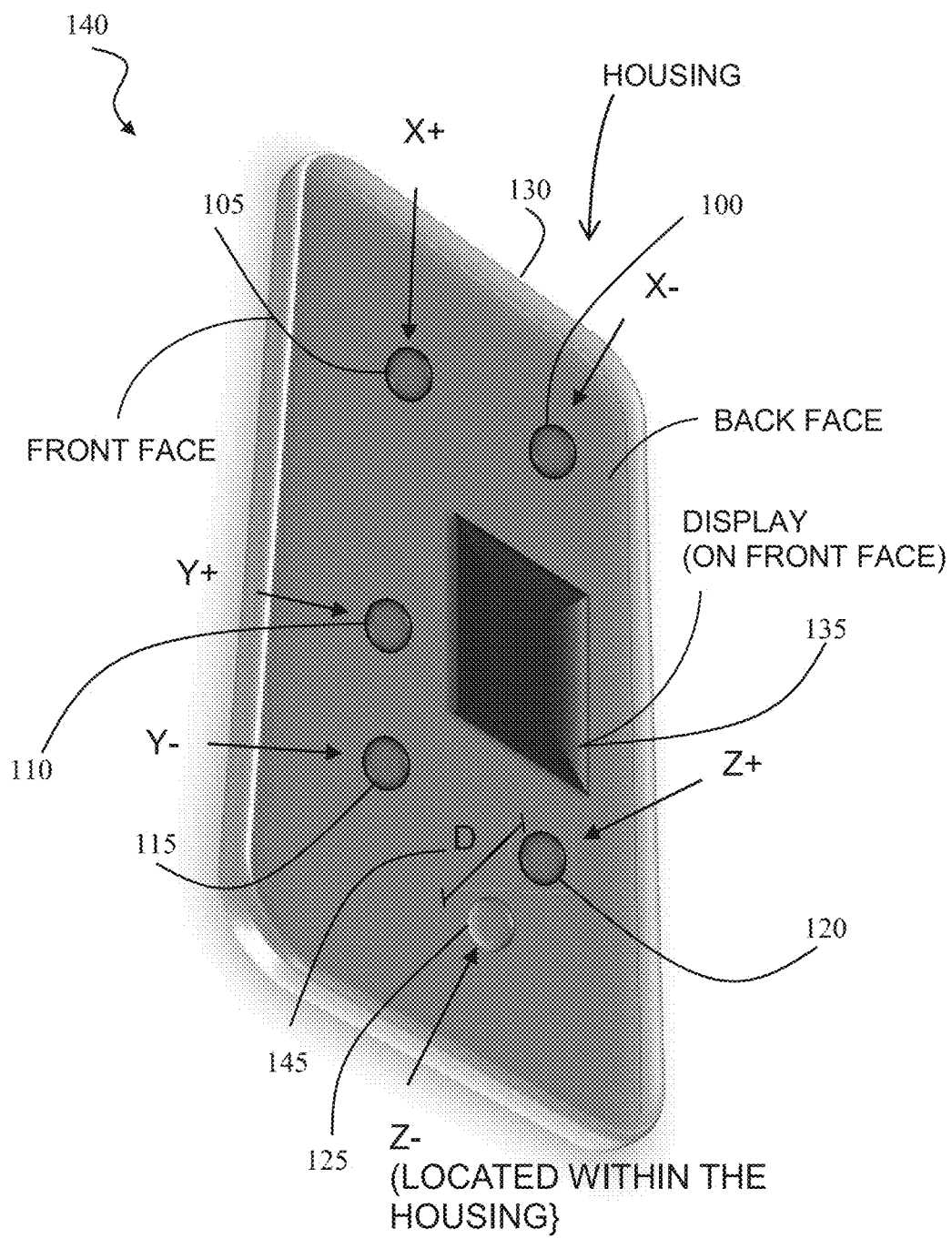
FIG. 5B is perspective view of an optimized external integrated VCG with a capacitively coupled Z-lead showing the front and back faces of the device, in accordance with an embodiment of the present invention.

In an additional embodiment, with reference to FIG. 5B, the second Z-axis electrode 125 may also be incorporated into the housing 130 and separated from the first Z-axis electrode to provide a pair of substantially orthogonal Z-axis electrodes utilizing capacitive coupling. In this embodiment, the integrated VCG device 140 comprises a pair of substantially orthogonal X-axis electrodes 100, 105, and a pair of substantially orthogonal Y-axis electrodes 110, 115 contained within a housing 130 and positioned on a substantially planar back surface of the housing 130. In this embodiment, a first Z-axis electrode 120 and the second Z-axis electrode 125 are both contained within the housing 130, wherein the first Z-axis electrode 120 is positioned on the back surface of the housing 130 and the second Z-axis electrode 125 is positioned within the interior of the housing 130, or alternatively, on the front surface of the housing 130, and separated from the first Z-axis electrode by a predetermined distance 145 to establish capacitive coupling between the Z-axis electrodes 120, 125. In operation, the integrated VCG device 140 is placed in contact with the chest of the patient at a proper measurement position such that the X-axis electrodes 100, 105, the Y-axis electrodes 110, 115 and the first Z-axis electrode 120 are in contact with the skin of the patient. The placement of the X-axis electrodes and the Y-axis electrodes, and the capacitive coupling of the Z-axis electrodes, is effective in collecting the cardiac electrical signals of the patient when placed in a measurement position. The housing 130 may further include a display 135 on a substantially planar front surface of the device 130.

The distance between the Z-axis electrodes may be established by fabricating the integrated VCG device housing 130 to be slightly thicker than the integrated VCG device illustrated in FIG. 5A, wherein the second Z-axis electrode that is external to the device. By incorporating both Z-axis electrodes into the slightly thicker housing 130 of the VCG device 140, non-contact, capacitive coupling between the second Z-axis electrode 125 and the first Z-axis electrode 120 that is in contact with the body tissue can be utilized to measure the Z-axis of the VCG signal. The predetermined distance 145 between the Z+ 120 and Z− 125 electrodes is estimated to be in the range of about 5 cm to about 2 cm, to provide the required signal through capacitive coupling. As such, the first Z-axis electrode 125 in combination with the second Z-axis electrode 130 acquires the cardiac signal from the body tissue without needing to establish contact between the second Z-axis electrode 130 and the body tissue. The advantage of this embodiment is that are no wired leads that are required to be placed on the body tissue external to the integrated VCG device 140, thereby allowing for a much less obtrusive, fully integrated, portable integrated VCG device 140 that allows for continuous remote monitoring of the patients ECG functions.

In a particular embodiment, the housing 130 of the integrated VCG device 140 may be a shielded enclosure with dimensions of approximately 9.65 cm×6.35 cm. However, this is not intended to be limiting and smaller dimensions of the housing are within the scope of the present invention.

Figure 6:
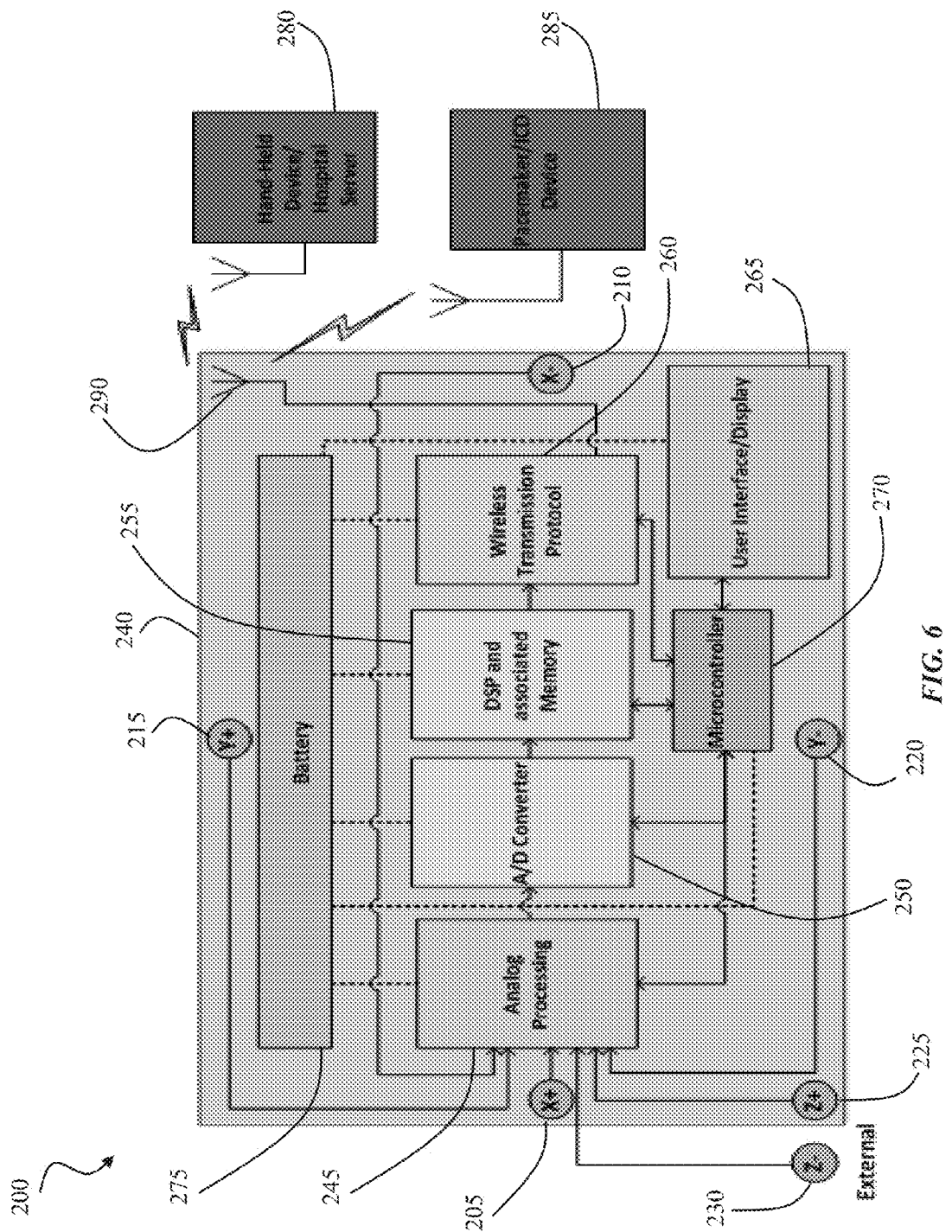
FIG. 6 is a functional block diagram of an integrated VCG with external Z lead, in accordance with an embodiment of the present invention.

With reference to FIG. 6, a functional block diagram representation of an external integrated VCG device 200 is illustrated. In this embodiment, "external" is used to refer to an embodiment of the VCG device 200 that is adapted to be positioned in a measurement position on the skin surface of a patient. In this embodiment, the X-axis electrodes 205, 210, the Y-axis electrodes 215, 220 and one of the Z-axis electrodes 225 are integrated into the housing 140 and are positioned on a back surface of the housing 140 to establish contact with the skin of a patient. The other Z-axis electrode 230 is connected to the device 200 by an external wire and is placed on the back (or other suitable location) of the human body, as previously described. This single external Z-axis electrode 230 may be held in place using a bandage, strap or any other device designed to hold the electrode 230 in place on the patient's back. In one embodiment of the invention, the wire and single Z-axis electrode 230 may be integrated within a strap, such as a single strap, that can be securely fastened around the patient's chest and back. Thus, the number of wires required to monitor a patient's individual cardiac rhythm is significantly reduced over the current 12-lead ECG machines. Using a strap to hold the electrode 230 for the Z-axis in place can be used for ambulatory, in-patient and out-patient monitoring allowing for greater comfort and mobility for the patient.

The integrated VCG device 200 may further include analog processing circuitry 245. The analog processing circuitry receives the signals on the six (6) X, Y and Z leads and may pass the signals through a differential amplifier and subsequently through a band-pass filter to remove high frequency noise. The amplified and filtered signals may then be passed through a buffer amplifier of the analog processing circuitry 245 to optimally match impedance with an analog-to-digital (A/D) converter 250. As such, the amplified, band-pass signals are converted into high-resolution digital data at the A/D converter 250. In this embodiment of FIG. 6, the analog-to-digital converter 250 is integrated into the integrated VCG device 240.

Following the conversion of the analog signals acquired by the electrodes to digital data at the A/D converter 250, the digital data may be stored in a memory and/or transmitted to a digital signal processor 255 for further processing. The digital signal processor 255 may include hardware and software for performing various signal processing functions, such as removal of residual 60 Hz power-line noise, adaptive filtering functions to recalibrate and re-orthogonalize the electrodes and transformation of the 3-lead VCG signal data to a 12-lead ECG.

The integrated VCG device 200 may further include telemetry circuitry 260, which may be embodied as a wireless transmission protocol. The telemetry circuitry 260 may receive the digital data from the digital signal processor 255 and may wirelessly transmit the digital data to a personal device or to a server 280. In a particular embodiment, the telemetry circuitry 260 may be a wireless communication system using an appropriate protocol (e.g., BLUETOOTH, BLUETOOTH low-energy, ZigBee, WiFi, etc.) that receives the processed data from the digital signal processor 255 and transmits the integrated VCG device 200 information, diagnoses, data analysis reports, etc. through an internal antenna 290. Considering a sampling rate of 1 KHz, and a 12-bit analog-to-digital converter, a nominal bit rate of 36 Kbps may be suitable for transmitting the three VCG signals, although other rates are within the scope of the present invention. Such a data rate, along with the necessary protocol and control and management overhead, can easily be accommodated by a Bluetooth Low Energy wireless module that can support rates up to 1 Mbps. In order to provide security between two communicating entities, the protocol may be used to provide encryption and authentication. The receiver of this data can be any unit desired by the user, for example an electronic device (e.g., computer, smartphone, tablet, hand-held device) connected wirelessly, a hospital server connected through a Wireless Local Area Network (WLAN), a cellular network or a combination of devices. Upon transfer of the integrated VCG information to the electronic device, the electronic device can monitor the information in real-time and/or use the infomation for further processing. In addition, the external integrated VCG device 200 can also exchange intelligent information with a pacemaker or other implantable Cardioverter/Defibriliator device 285.

The integrated VCG device 200 may further include a microcontroller 270 in communication with the analog processing circuitry, the A/D converter 250, the digital signal processor and associated memory 255 and the telemetry circuitry 260. The microcontroller is in communication with the digital signal processor 255 and may be configured to drive the user interface/display 265 that can be used to query the integrated VCG system for information/diagnoses, to adjust settings, to reprogram the system and to toggle between various modes (e.g., 6-lead mode, sleep mode, ICU mode, training mode, etc.). Additionally, the digital signal processor 255 and microcontroller 270, and/or associated circuitry, will also contain a trainable learning system that analyzes the VCG data, learns various VCG patterns, and outputs useful information and diagnoses for the patient.

Figure 7:
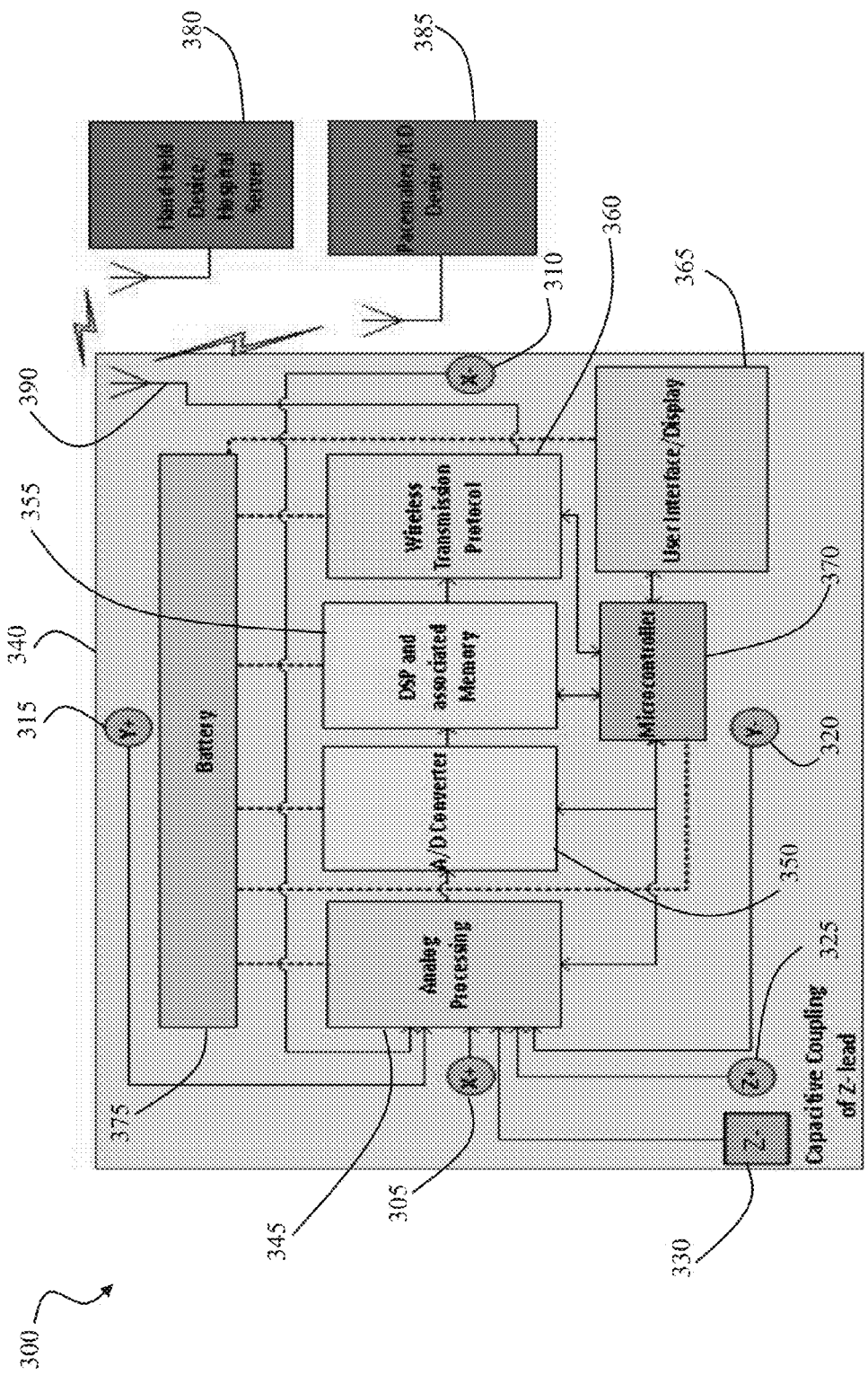
FIG. 7 is a functional block diagram of an optimized external integrated VCG with a capacitively coupled Z-lead, in accordance with an embodiment of the present invention.
Figure 8:
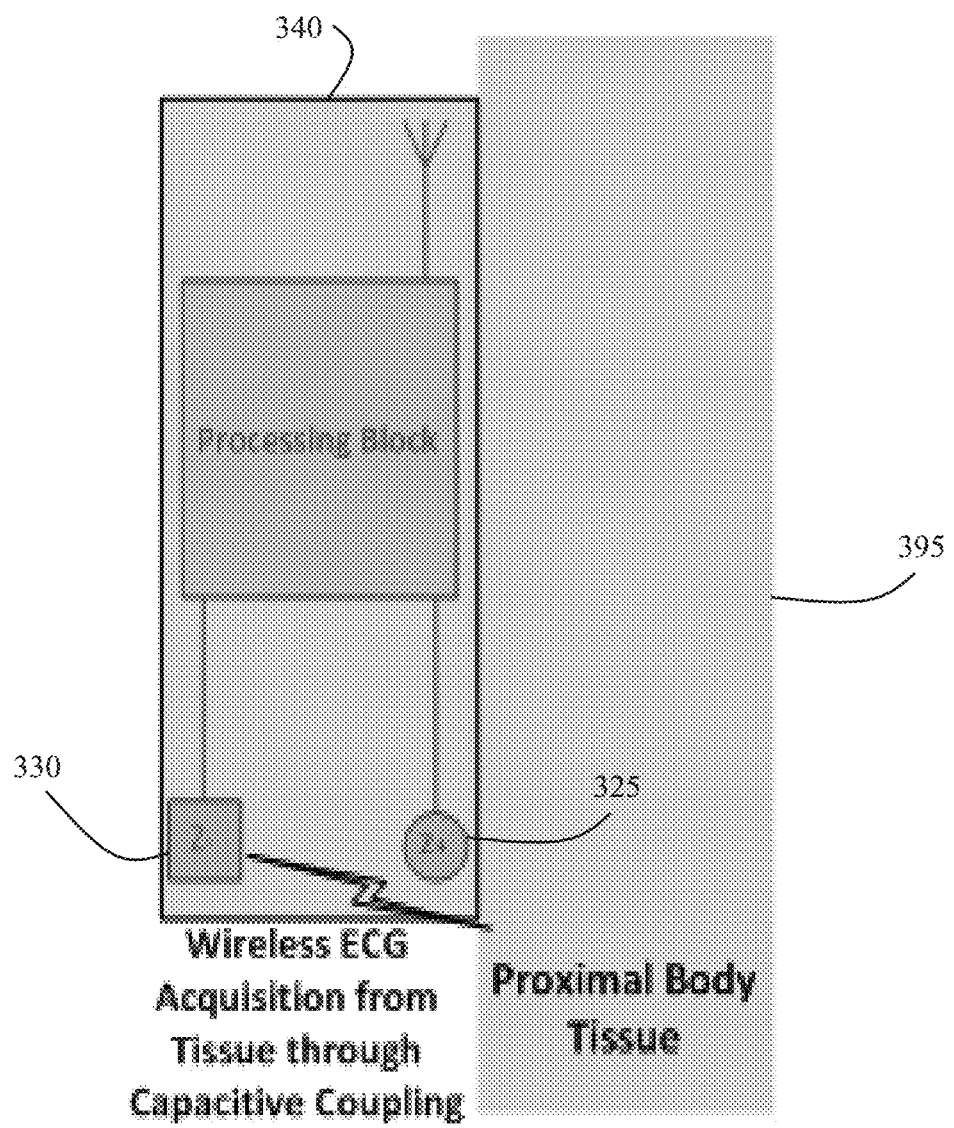
FIG. 8 is a side view of an optimized external integrated VCG showing the Z-lead acquiring the cardiac signals wirelessly through capacitive coupling in accordance with an embodiment of the present invention.

With reference to FIG. 7, a functional block diagram representation of an external integrated VCG device 300 having an integrated second Z-axis electrode is illustrated. In this embodiment, "external" is used to refer to an embodiment of the integrated VCG device 300 that is adapted to be positioned in a measurement position on the skin surface of a patient. In this embodiment, the X-axis electrodes 305, 310, the Y-axis electrodes 315, 320 and both of the Z-axis electrodes 325, 330 are integrated into the housing 340 and are positioned on a back surface of the housing 340 to establish contact with the skin of a patient. As shown with reference to FIG. 8, in this embodiment, the positive Z-axis electrode 325 is separated from the negative Z-axis electrode 330, in the Z-axis direction, by a predetermined distance that is established within the housing 340. In one embodiment, one of the Z-axis electrodes 325 may be positioned on a back surface of the housing 340 and the other Z-axis electrode 330 may be positioned on, or near, a front surface of the housing 340 to establish the predetermined distance between the Z-axis electrodes 325, 330. In a particular embodiment, the inter-electrode distance between the Z-axis electrodes 325, 330 may be about 1 cm. The separation between the Z-axis electrodes 325, 330 allows for acquisition of the VCG signal from the proximal body tissue 395 utilizing capacitive coupling. As such, in this embodiment, all of the electrodes necessary to acquire the VCG signal are contained within the housing 340. Thus, all of the external wires required to monitor a patient's individual cardiac rhythm are eliminated, in comparison with the 12 leads required in conventional 12-lead ECG machines. A strap may be used to secure the device 300 to the body of the patient, or alternatively, the back surface of the device 300 may include a substance that allows for removable adherence to the surface of patient's skin. The device 300 having integrated electrodes is advantageous for use for ambulatory, in-patient and out-patient monitoring allowing for greater comfort and mobility for the patient.

The integrated VCG device 300 may further include analog processing circuitry 345. The analog processing circuitry receives the signals on the six (6) X, Y and Z leads and may pass the signals through a differential amplifier and subsequently through a band-pass filter to remove high frequency noise. The amplified and filtered signals may then be passed through a buffer amplifier of the analog processing circuitry 345 to optimally match impedance with an analog-to-digital (A/D) converter 350. As such, the amplified, band-pass signals are converted into high-resolution digital data at the A/D converter 350. in this embodiment of FIG. 6, the analog-to-digital converter 250 is integrated into the VCG device 350.

Following the conversion of the analog signals acquired by the electrodes to digital data at the A/D converter 350, the digital data may be stored in a memory and/or transmitted to a digital signal processor 355 for further processing. The digital signal processor 355 may include hardware and software for performing various signal processing functions, such as removal of residual 60 Hz power-line noise, adaptive filtering functions to recalibrate and re-orthogonalize the electrodes and transformation of the 3-lead VCG signal data to a 12-lead ECG.

The integrated VCG device 300 may further include telemetry circuitry 360, which may be embodied as a wireless transmission protocol. The telemetry circuitry 360 may receive the digital data from the digital signal processor 355 and may wirelessly transmit the digital data to a personal device or to a server 380. In a particular embodiment, the telemetry circuitry 360 may be wireless communication system comprising an appropriate protocol (e.g. BLUETOOTH, BLUETOOTH low-energy, ZigBee, WiFi, etc. ) that receives the processed data from the digital signal processor 355 and transmits the integrated VCG device 300 information, diagnoses, data analysis reports, etc. through an internal antenna 390. Considering a sampling rate of 1 KHz, and a 12-bit analog-to-digital converter, a nominal bit rate of 36 Kbps may be suitable for transmitting the three VCG signals, although other rates are within the scope of the present invention. Such a data rate, along with the necessary protocol and control and management overhead, can easily be accommodated by a Bluetooth Low Energy wireless module that can support rates up to 1 Mbps. In order to provide security between two communicating entities, the protocol may be used to provide encryption and authentication. The receiver of this data can be any unit desired by the user, for example an electronic device (e.g., computer, smartphone, tablet, hand-held device) connected wirelessly, a hospital server connected through a Wireless Local Area Network (WLAN), a cellular network or a combination of devices. Upon transfer of the integrated VCG information to the electronic device, the electronic device can monitor the information in real-time and/or use the information for further processing. In addition, the external integrated VCG device 300 can also exchange intelligent information with a pacemaker or other implantable Cardioverter/Defibrillator device 385.

The integrated VCG device 300 may further include a microcontroller 370 in communication with the analog processing circuitry, the A/D converter 350, the digital signal processor and associated memory 355 and the telemetry circuitry 360. The microcontroller is in communication with the digital signal processor 355 and may be configured to drive the user interface/display 365 that can be used to query the integrated VCG system for information/diagnoses, to adjust settings, to reprogram the system and to toggle between various modes (e.g., 6-lead mode, sleep mode, ICU mode, training mode, etc. ). Additionally, the digital signal processor 355 and microcontroller 370, and/or associated circuitry, will also contain a trainable machine learning system that analyzes the VCG data, learns various VCG patterns, and outputs useful information and diagnoses concerning the patient.

Figure 9:
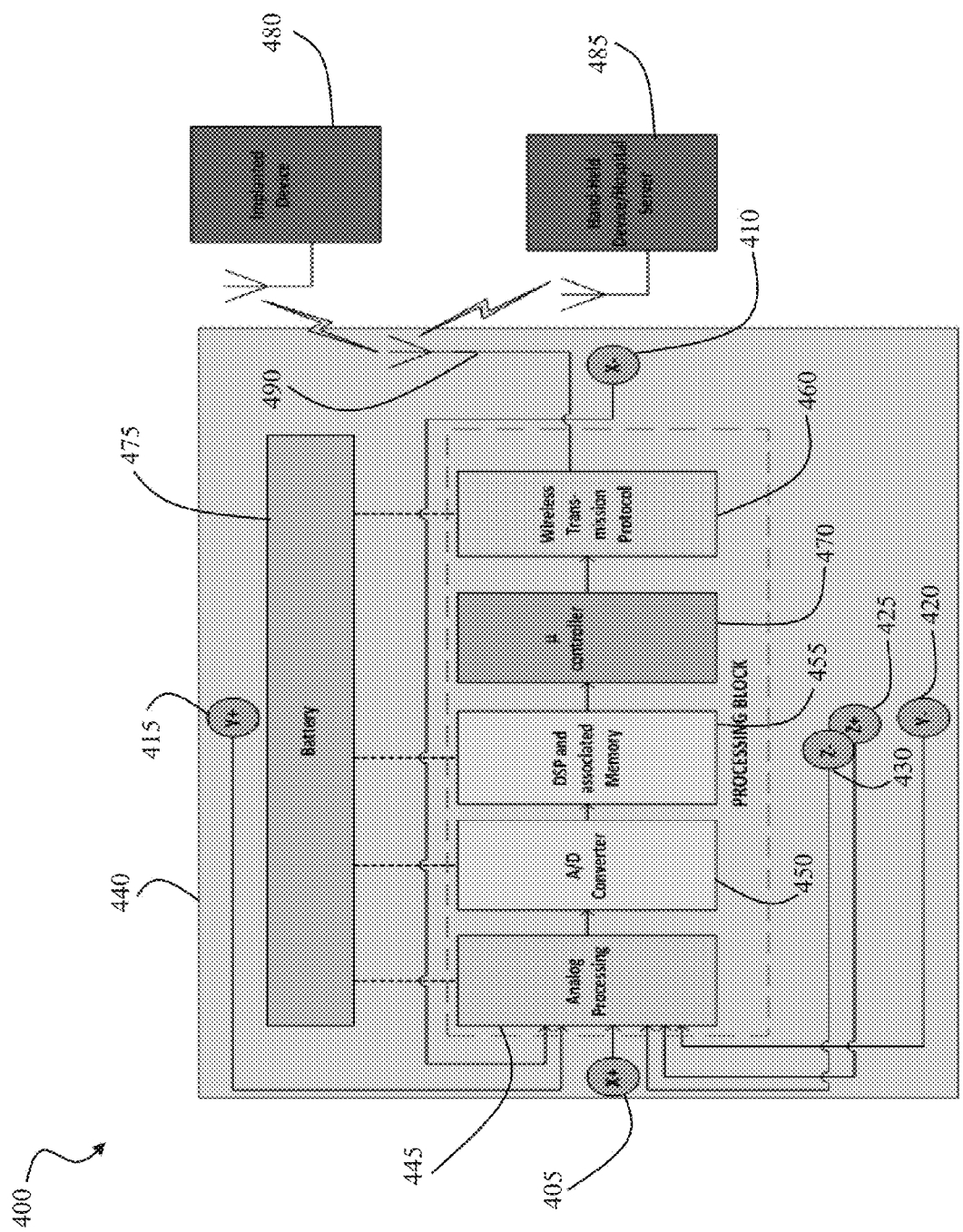
FIG. 9 is a functional block diagram of an internal integrated VCG, in accordance with an embodiment of the present invention.
Figure 10:
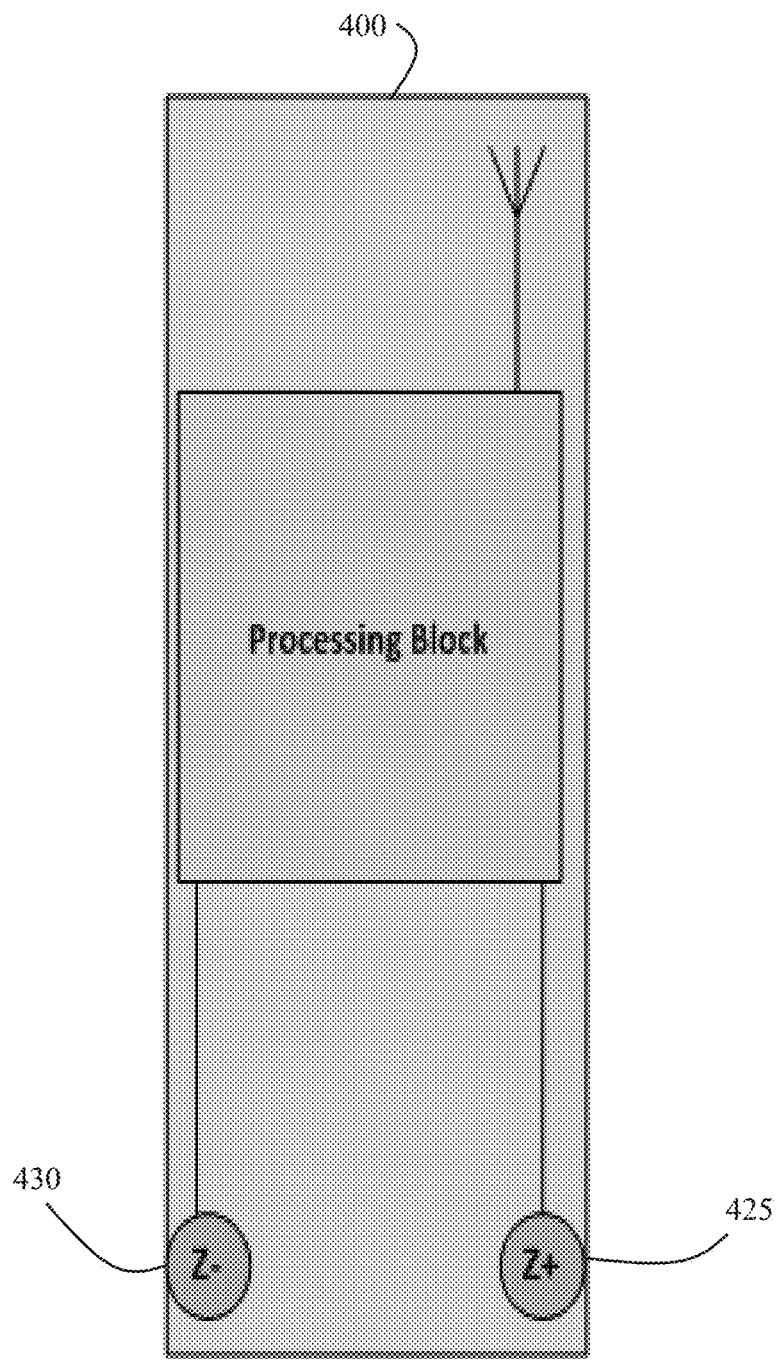
FIG. 10 is a side view of an internal integrated VCG showing the Z-leads separated by the indicated depth, in accordance with an embodiment of the present invention.

With reference to FIG. 9, a functional block diagram representation of an internal integrated VCG device 400 having an integrated second Z-axis electrode is illustrated. In this embodiment, "internal" is used to refer to an embodiment of the VCG device 400 that is adapted to be implanted in the chest area of the patient. In this embodiment, the X-axis electrodes 405, 410, the Y-axis electrodes 415, 420 and both of the Z-axis electrodes 425, 430 are integrated into the housing 440 or adhered to the back surface of the housing 440. to establish contact with the skin of a patient. As shown with reference to FIG. 9, in this embodiment, the positive Z-axis electrode 425 is separated from the negative Z-axis electrode 430, in the Z-axis direction, by a predetermined distance that is established within the housing 440. In one embodiment, one of the Z-axis electrodes 425 may be positioned on a back surface of the housing 440 and the other Z-axis electrode 430 may be positioned on, or near, a front surface of the housing 440 to establish the predetermined distance between the Z-axis electrodes 425, 430. In a particular embodiment, the inter-electrode distance between the Z-axis electrodes 425, 430 may be about 1 cm. The separation between the Z-axis electrodes 425, 430 allows for acquisition of the VCG signal with direct contact with body tissue. As illustrated with reference to FIG. 10, in which a side view of the integrated VCG device 400 is shown, the separation of the Z-axis leads 425, 430 in this embodiment allows the device to collect cardiac signals from the nearby tissue when the vectorcardiogram device 400 is implanted into the body of the patient. In one such an embodiment, the tissue can be separated by a maximum distance equal to the thickness of the implanted VCG device 400 and is sufficient to obtain a comprehensible signal in the body environment. As such, in this embodiment, all of the electrodes necessary to acquire the VCG signal are contained within the housing 440. Thus, all of the external wires required to monitor a patient's individual cardiac rhythm are eliminated, in comparison with the 12 leads required in conventional 12-lead ECG machines. The implanted device 400 having integrated electrodes is advantageous for use in out-patient monitoring of the patient.

The integrated VCG device 400 may further include analog processing circuitry 445. The analog processing circuitry receives the signals on the six (6) X, Y and Z leads and may pass the signals through a differential amplifier and subsequently through a band-pass filter to remove high frequency noise. The amplified and filtered signals may then be passed through a buffer amplifier of the analog processing circuitry 445 to optimally match impedance with an analog-to-digital (A/D) converter 450. As such, the amplified, band-pass signals are converted into high-resolution digital data at the A/D converter 450. In this embodiment of FIG. 9, the analog-to-digital converter 450 is integrated into the VCG device 450

Following the conversion of the analog signals acquired by the electrodes to digital data at the A/D converter 450, the digital data may be stored in a memory and/or transmitted to a digital signal processor 455 for further processing. The digital signal processor 455 may include hardware and software for performing various signal processing functions, such as removal of residual 60 Hz power-line noise, adaptive filtering functions to recalibrate and re-orthogonal ize the electrodes and transformation of the 3-lead VCG signal data to a 12-lead ECG.

The integrated VCG device 400 may further include telemetry circuitry 460, which may be embodied as a wireless transmission protocol. The telemetry circuitry 460 may receive the digital data from the digital signal processor 455 and may wirelessly transmit the digital data to a personal device or to a server 480. In a particular embodiment, the telemetry circuitry 460 may be wireless communication system comprising an appropriate protocol (e.g., BLUETOOTH, BLUETOOTH low-energy, ZigBee, WiFi, etc.) that receives the processed data from the digital signal processor 455 and transmits the integrated VCG device 400 information, diagnoses, data analysis reports, etc. through an internal antenna 490. Considering a sampling rate of 1 KHz, and a 12-bit analog-to-digital converter, a nominal bit rate of 36 Kbps may be suitable for transmitting the three VCG signals, although other rates are within the scope of the present invention. Such a data rate, along with the necessary protocol and control and management overhead, can easily be accommodated by a Bluetooth Low Energy wireless module that can support rates up to 1 Mbps. In order to provide security between two communicating entities, the protocol may be used to provide encryption and authentication. The receiver of this data can be any unit desired by the user, for example an electronic device (e.g., computer, smartphone, tablet, hand-held device) connected wirelessly, a hospital server connected through a Wireless Local Area Network (WLAN), a cellular network or a combination of devices. Upon transfer of the integrated VCG information to the electronic device, the electronic device can monitor the information in real-time and/or use the information for further processing. In addition, the external integrated VCG device 400 can also exchange intelligent information with a pacemaker or other implantable Cardioverter/Defibrillator device 485.

The integrated VCG device 400 may further include a microcontroller 470 in communication with the analog processing circuitry, the A/D converter 450, the digital signal processor and associated memory 455 and the telemetry circuitry 460. In the present invention, digital signal processing can be used to reduce or eliminate spurious effects via amplification of weak signals, filtering, and adaptive signal cancellation. Additionally, post-reception signal processing techniques may be used to compensate for degradation or distortion in the signal and to restore signal orthogonality. Additionally, in this embodiment, the user interface/display is removed from the device and the VCG device 400 may be controlled by a remote device that wirelessly communicates with the microcontroller 470 contained in the device 400. The remote device can be used to query the integrated VCG system for information/diagnoses, to adjust settings, to reprogram the system and to toggle between various modes (e.g., 6-lead mode, sleep mode, mode, training mode, etc. ). Additionally, the digital signal processor 455 and microcontroller 470, and/or associated circuitry, can also optionally contain a trainable learning system that analyzes the VCG data, learns various VCG patterns, and outputs useful information and diagnoses for the patient.

In an additional embodiment of the integrated VCG device of the invention, a 2-dimensional frontal plane VCG may be utilized instead of a 3-dimensional VCG. In this alternative embodiment, a pair of orthogonal X-axis electrodes and a pair of Y-axis electrodes may be incorporated into the housing and use to collect the electrical cardiac signals of the patient. In this embodiment, the Z-axis electrodes are eliminated and the information provided by the 2-dimensional frontal plane VCG is equivalent to at least 6 leads of the 12-lead ECG.

Embodiments of a miniaturized integrated VCG device, as described in the present invention, allows the necessary electronics and associated electrodes to fit into a single package that is small enough to be non-intrusive and that can be worn by the patient. Both the external and internal embodiments of the integrated VCG device may additionally include a battery to reduce the power line noise. Utilizing battery power for the device will eliminate the 60 Hz noise directly from the power source and additional filtering may be used to remove other 60 Hz noise resulting from electrical and magnetic coupling of the circuitry, as well as other noise, for example. In one embodiment, differential amplifiers for each dimension (X, Y and Z) may be incorporated in the analog processing circuitry to eliminate common-mode noise and the output of the amplifiers may be filtered using a 0.5-150 Hz band-pass filter to reduce thermal noise bandwidth. The filtered signals may then be passed through an oscilloscope with a built-in analog-to-digital A/D) converter to provide digital data representative of the collected VCG signals. During digital signal processing, the 60 Hz noise may be removed, orthogonality may be restored, the stored data may be processed, and the signal can be made available in real-time. Signal processing techniques may further remove noise elements and restore the loss of amplitude and orthogonality as sensors are moved closer together.

Figure 11A:
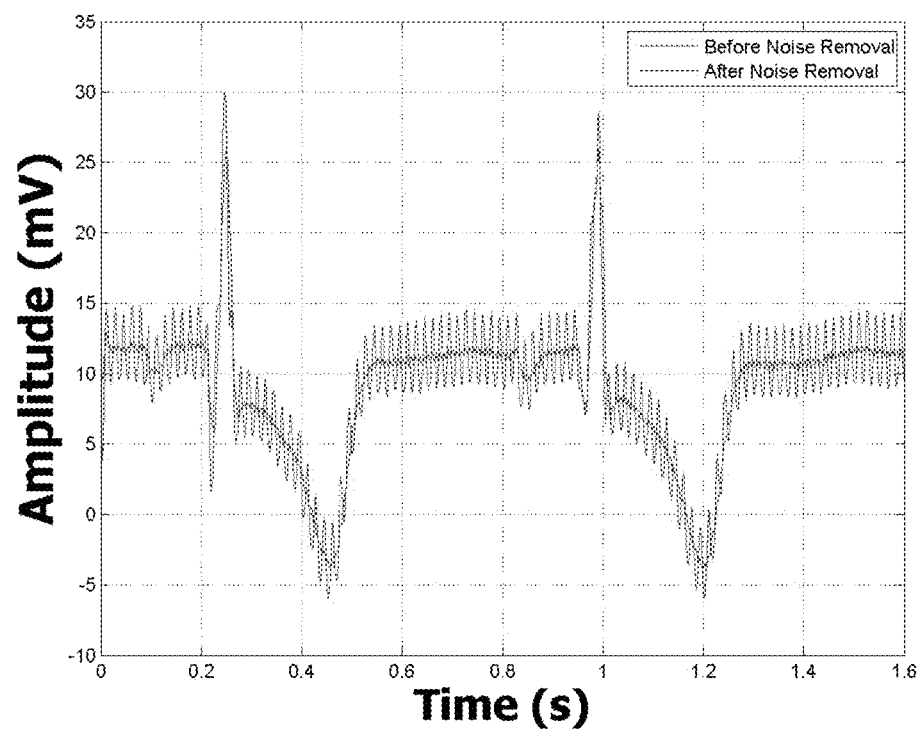
FIG. 11A shows the measured and noise filtered signal in the X-axis for the measured distance between a pair of electrodes, X=1.8 cm, in accordance with an embodiment of the present invention.

FIG. 11A illustrates the measured signal, before noise removal, and the filtered signal, after noise removal, for the X-axis at a distance between the pair of electrodes equal to about 1.8 cm. In this embodiment, the circuit is battery powered, analog filtered and shielded to reduce a majority of the noise, but noise filtering or cancellation is still typically necessary. In an exemplary embodiment, MATLAB code may be used to remove 60 Hz power line noise and other noise either via filtering or adaptive filtering. As seen, the post-processing block helps to remove the 60 Hz noise and other unwanted signals, as the ECG measurements with 60 Hz noise is input to the MATLAB-based filtering utilizing a second order IIR (infinite impulse response) notch filter. Thus, the noise can be removed, as illustrated with reference to FIG. 11A. The algorithm used to filter the signal may be designed such that the integrated VCG device will be sensitive to the specific spectral content of the ECG signal around 60 Hz and may additionally be trained to adaptively learn and cancel "noise" at other frequencies, or alternatively set to 50 Hz in certain countries.

Figure 11B:
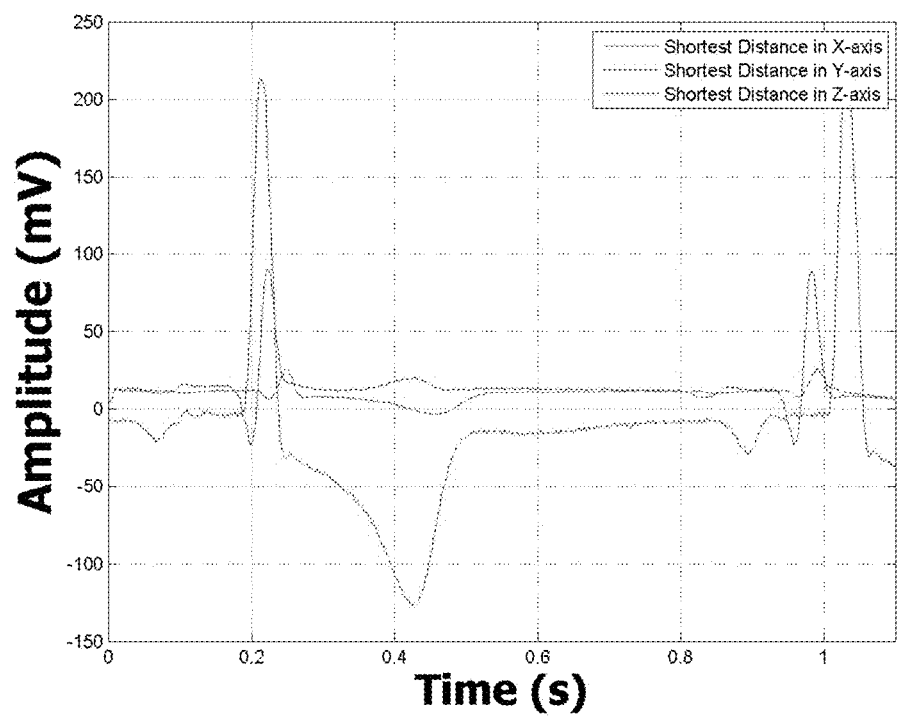
FIG. 11B shows filtered signals for the measured distances of 1.8 cm in X axis and 2.2 cm in Y axis and Z axis, in accordance with an embodiment of the present invention.
Figure 12:
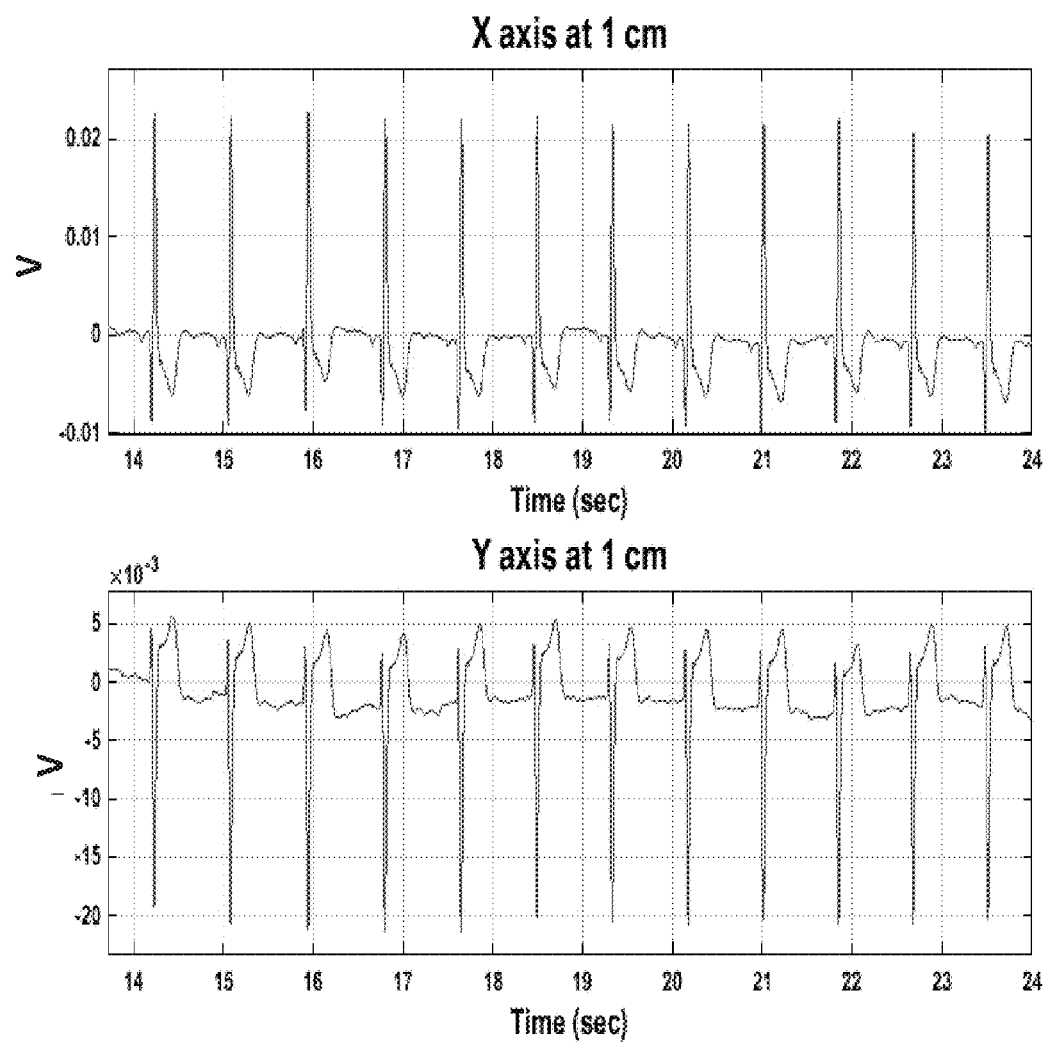
FIG. 12 shows the X, Y and Z tracing acquired simultaneously with an experimental multi-lead external integrated VCG at a distance of 1 cm between electrodes in both X and Y directions, in accordance with an embodiment of the present invention.

The filtered signals for the shortest distances in the X-axis (1.8 cm), Y-axis (2.2 cm), and Z-axes are illustrated with reference to FIG. 11B. As shown in FIG. 11B, the amplitude of the signal in the Z-axis is larger than the X-axes and Y-axes because the distance between the Z-axis leads is very large compared to the inter-electrode distance in the X-axis and the Y-axis, considering that one of the Z-axis electrodes was placed on the back of the patient. FIG. 12 shows the plots of the X and Y leads where the electrodes were placed 1 cm apart.

Figure 13A:
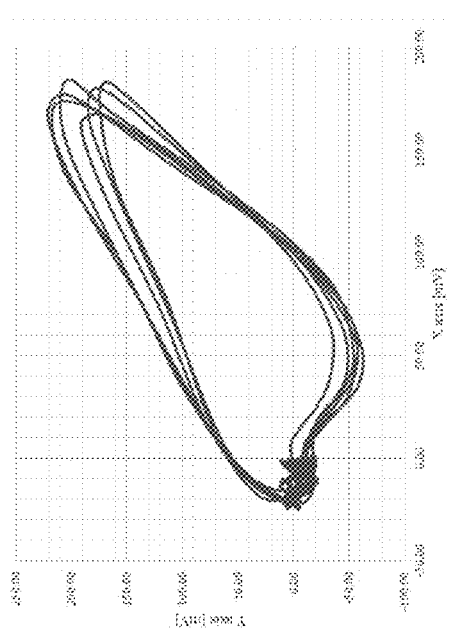
FIG. 13A shows the integrated VCG loops plotted in coronal (X-Y) plane, in accordance with an embodiment of the present invention.
Figure 13B:
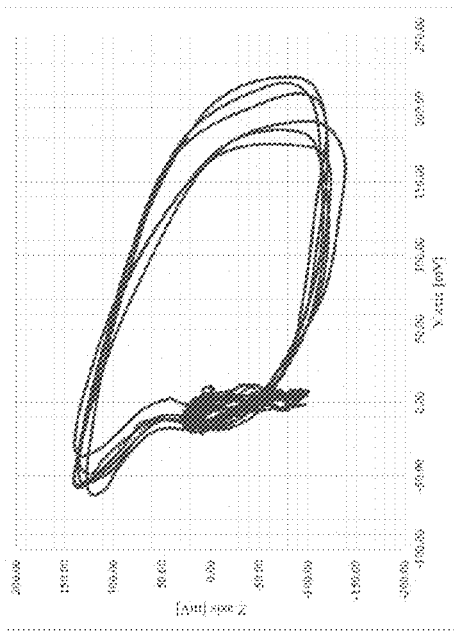
FIG. 13B shows the integrated VCG loops plotted in sagittal (Y-Z) plane, in accordance with an embodiment of the present invention.
Figure 13C:
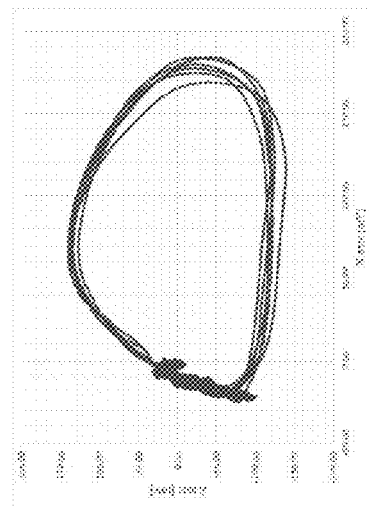
FIG. 13C shows the integrated VCG loops plotted in transverse (X-Z) plane, in accordance with an embodiment of the present invention.
Figure 14:
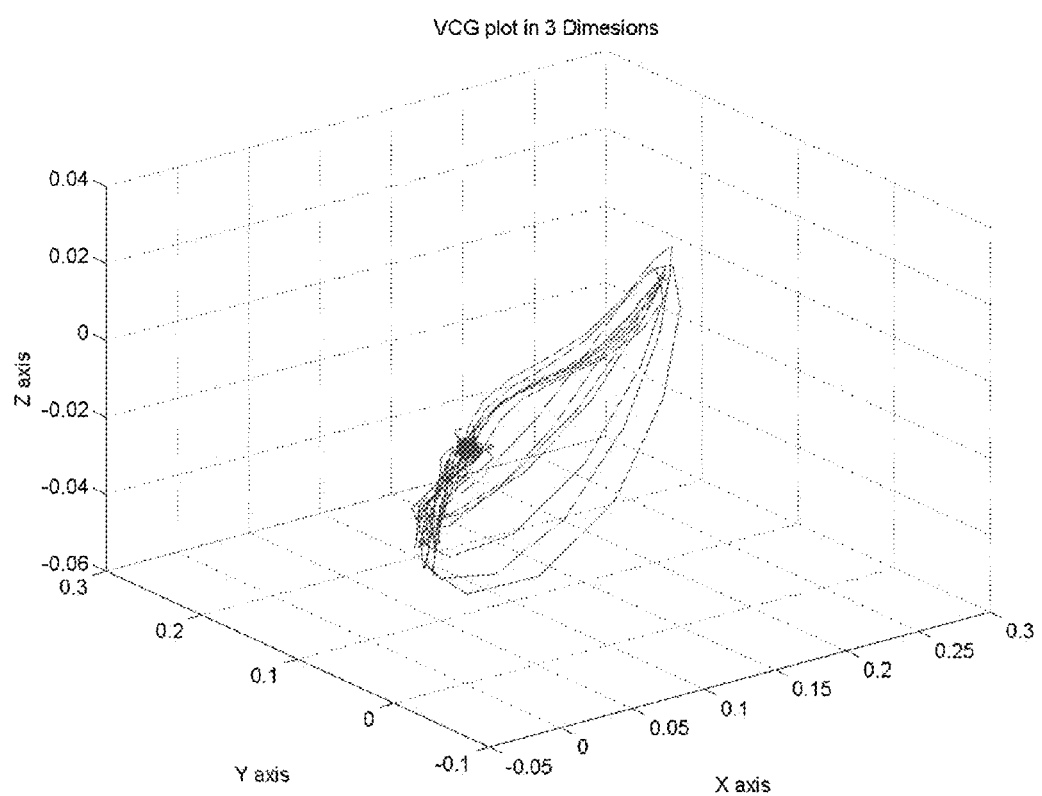
FIG. 14 shows the integrated VCG loops plotted in three dimensions as the cardiac vector trajectory, in accordance with an embodiment of the present invention.

FIG. 13A illustrates a plot of the VCG loops based upon the acquired cardiac vector projected in the X-Y plane. FIG. 13B illustrates a plot of the VCG loop based upon the acquired cardiac vector projected in the Y-Z plane and FIG. 13C illustrates a plot of the VCG loop based upon the acquired cardiac vector projected in the X-Z. FIG. 14 illustrates the VCG loops plotted in three dimensions based upon the VCP loops shown in FIGS. 13A, 13B and 13C.

Post-reception signal processing techniques can additionally be used to convert the 3-lead VCG signals to the 12-lead ECG that is more familiar to physicians. There is a linear relationship between the 3-lead VCG signals and each of the 12-lead ECG signals. Hence, there is a 12×3 transformation matrix that converts the 3-lead VCG vector to the 12-lead ECG. In one embodiment, the digital signal processor of the integrated VCG device of the present invention may implement adaptive filtering techniques, such as those employing a least-squares algorithm, a least-mean-squares (LMS) algorithm or a recursive least-squares algorithm (RLS) to learn the 12×3 transformation matrix that is unique to the specific patient.

Because the human chest is not truly planar in shape, the X and Y axes may be inclined, thereby causing the VCG leads to lose orthogonality. The angle of inclination depends upon the body type of the patient and cannot be estimated prior to installation of the integrated VCG device. By using the 12-lead ECG the angles of inclination can be calculated and orthogonality can be restored via software implemented in the digital signal processor. In an exemplary embodiment, at the time of fitting of the 3-lead VCG device, the patient may also be fitted with a standard 12-lead ECG. The 3-lead VCG device and the 12-lead ECG machine may be synchronized and used to read the cardiac signals (VCG and ECG) of the patient, substantially simultaneously. The ECG leads may then be removed from the patient, leaving the integrated VCG device in place. The cardiac signals read by the integrated VCG and the ECG may then be transmitted to an external server or device to perform the calibration. The 12-lead ECG signals and a 3×12 inverse transformation matrix that is determined via research prior to the fitting of the VCG device, are used to calibrate the integrated VCG device. It is envisioned that the inverse transformation matrix will be applicable to all body types and can therefore be employed for all patients. However, in an alternative embodiment, it may be necessary to determine multiple inverse transformation matrices that are unique to specifically identified body types to allow for adequate calibration of the integrated VCG device. The 3×12 inverse transformation matrix is applied to the 12-lead ECG signals to obtain a normal signal that is not distorted as a result of the curvature of the patient's chest. This normal signal is then compared with the signal measured from the integrated VCG device. The integrated VCG device is then corrected by rotating it by a quantity that minimizes the error between the normal signal and the integrated VCG signal. Following the calibration of the integrated VCG device, the corrected integrated VCG signal may then be then recorded and stored on the integrated VCG device as a reference cardiac vector.

If the integrated VCG device is external and in contact with the skin of the patient, the device can be removed by the patient at any time, such as to replace the batteries in the device. When the patient reattaches the device, it is likely that the placement of the device will be at least slightly different than the placement during the original fitting of the device performed by the physician. Further correction for any incorrect placement (by the patient) or inadvertent disorientation of the device can be performed to re-establish orthogonality via signal processing that rotates and or translates the VCG signal in software or by physically orienting the device. The reference cardiac vector that is stored in the VCG device, as previously described regarding the initial fitting of the integrated VCG device, may additionally be used as a reference for correcting distortion resulting from the subsequent misplacement of the device by the patient, principally in the form of incorrect orientation in the XY plane. The signal fidelity may suffer from incorrect placement of the VCG device. This incorrect placement may be characterized as an inadvertent rotation or translation from the correct orientation and location. A method that corrects the effects of such an inadvertent rotation in software, without requiring patient involvement, is provided by the present invention. The method utilizes the reference cardiac vector that was determined at the initial fitting to correct for the subsequent misplacement of the device. The cardiac vector from the rotated VCG recording is iteratively rotated (in software) in small angles such that the minimum mean square error (MMSE) between the disoriented cardiac vector and the reference cardiac vector is minimized.

In certain embodiments of the present invention, the digital signal processor of the integrated VCG system may be configured to adaptively learn the 12×3 matrix transformation that converts the VCG signal to the "gold standard" 12-lead ECG signal when the 3-lead VCG device is initially installed on the patient. The 12-lead ECG contains 12 signals (leads) commonly referred to as: I, II, III, aVR, aVL, aVF, V1, V2, V3, V4, V5, and V6. When the 12-lead ECG and the 3-lead VCG devices that are attached to the patient are synchronized, an adaptive signal processing technique may be used to process the transformation coefficients that are used to convert the 3-lead VCG signal to the 12-lead ECG. In one embodiment, each of the 12 measured ECG signals may be compared with each of the 3 measured VCG signals and the coefficients in the matrix transformation may be computed to achieve the best matching coefficients by minimizing the mean-squared error between each of the measured 12 ECG and the ECG signals derived from the 3-lead VCG signal.

Figure 15:
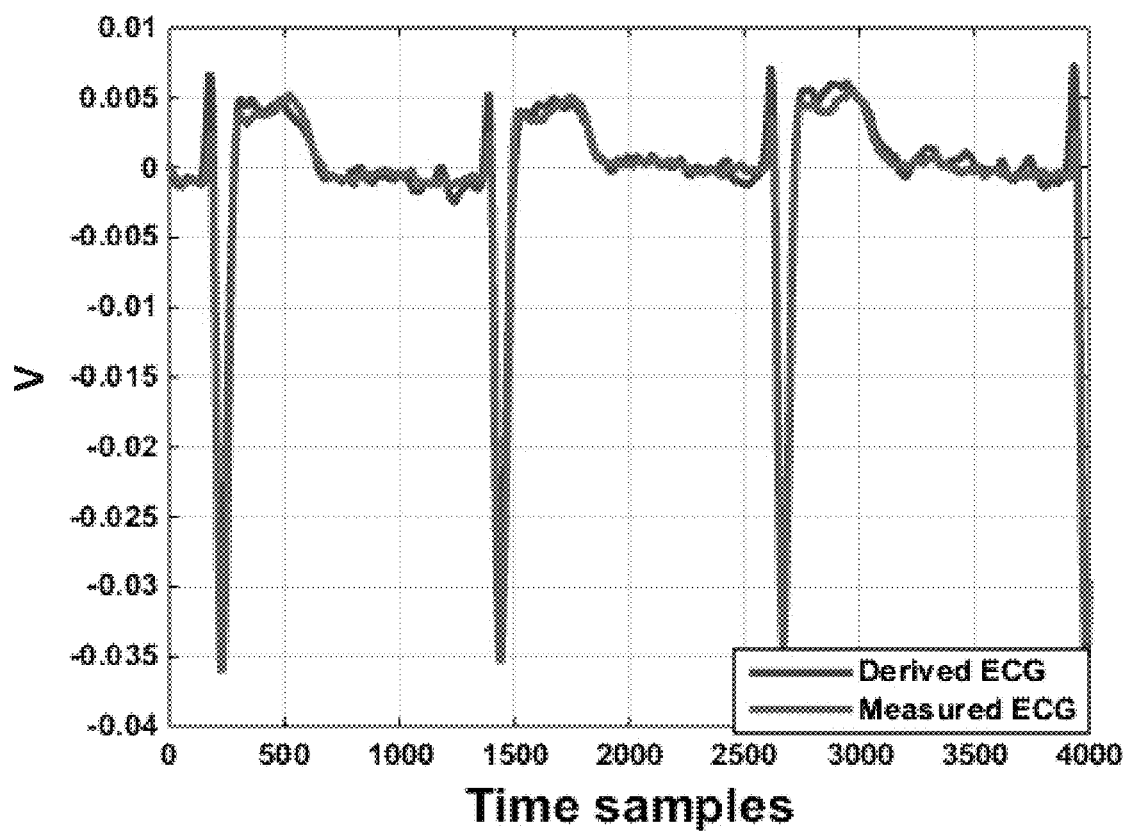
FIG. 15 shows measured lead aVF compared with aVF lead derived from integrated VCG leads, in accordance with an embodiment of the present invention.

The process required to obtain the transformation coefficients involves measuring the ECG and VCG leads simultaneously and obtaining the coefficients using a suitable algorithm. In an exemplar embodiment, the ECG leads corresponding to I, aVF, and V2 were measured with the X, Y and Z leads of the VCG device, substantially simultaneously. The least-square method was then employed to determine the transformation coefficients. FIG. 15 illustrates the measured ECG lead, aVF and the aVF lead derived from the VCG leads using the calculated transformation coefficients.

Figures 16A, 16B:
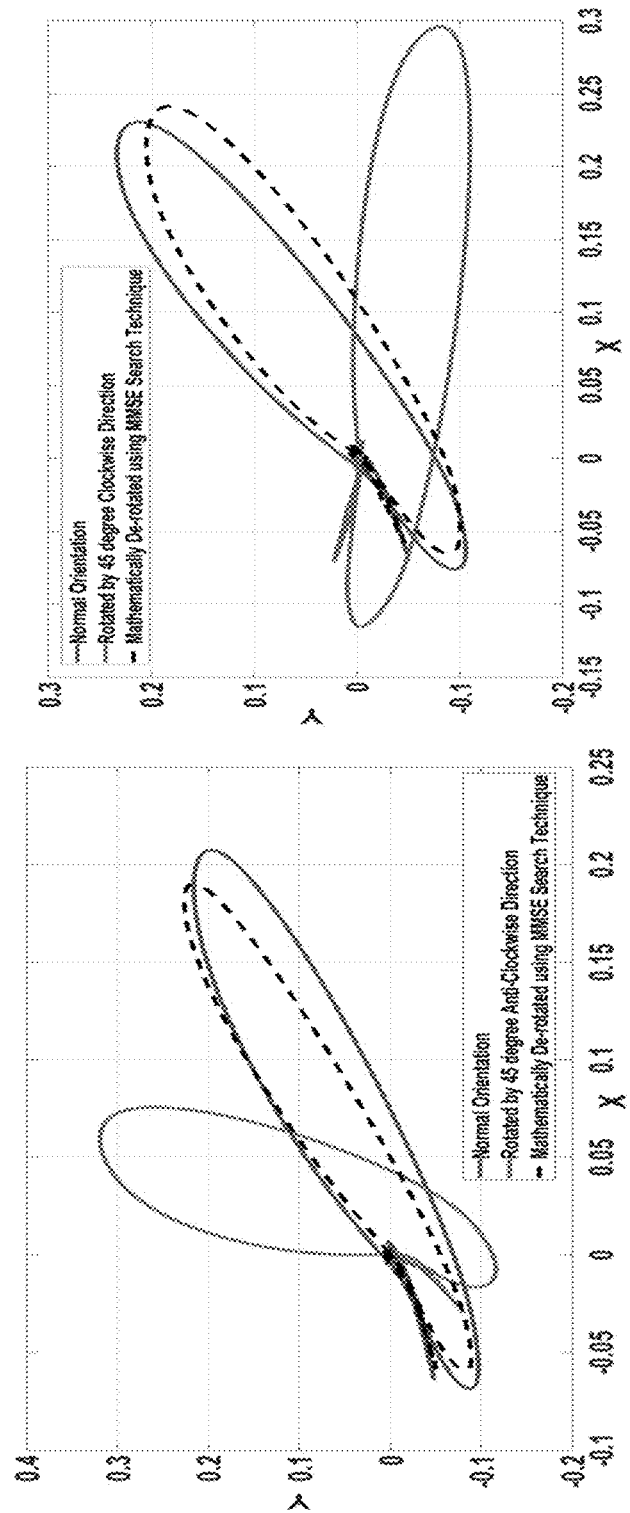
FIG. 16A shows the cardiac vector projected in the coronal (XY) Plane with integrated VCG device in normal orientation (blue), 45 degree anti-clockwise rotation (red), and de-rotated in software (black), in accordance with an embodiment of the present invention.
FIG. 16B shows the cardiac vector projected in the coronal (XY) Plane with integrated VCG device in normal orientation (blue), 45 degree clockwise rotation (red), and de-rotated in software (black), in accordance with an embodiment of the present invention.
Figure 17A:
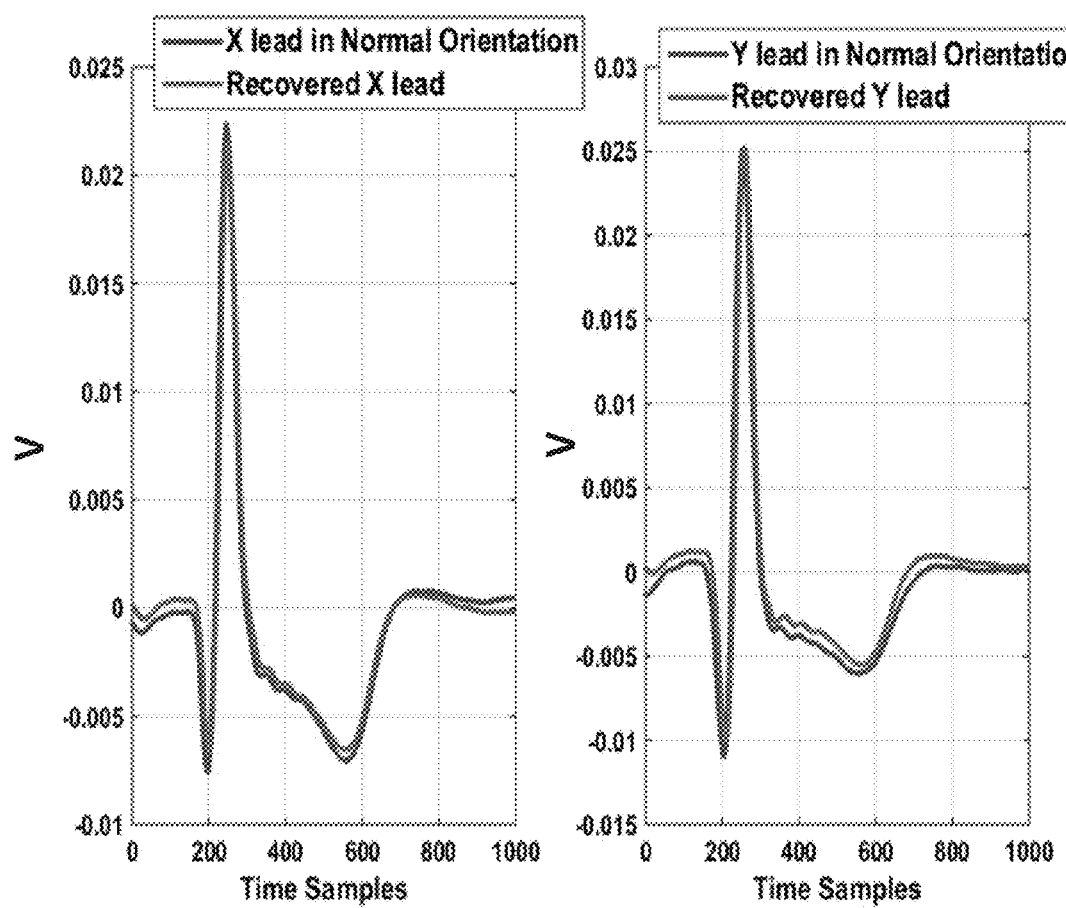
FIG. 17A shows the comparison of X and Y Leads recorded with normal electrode placement and software-recovered leads (electrodes were rotated in the anti-clockwise direction), in accordance with an embodiment of the present invention.
Figure 17B:
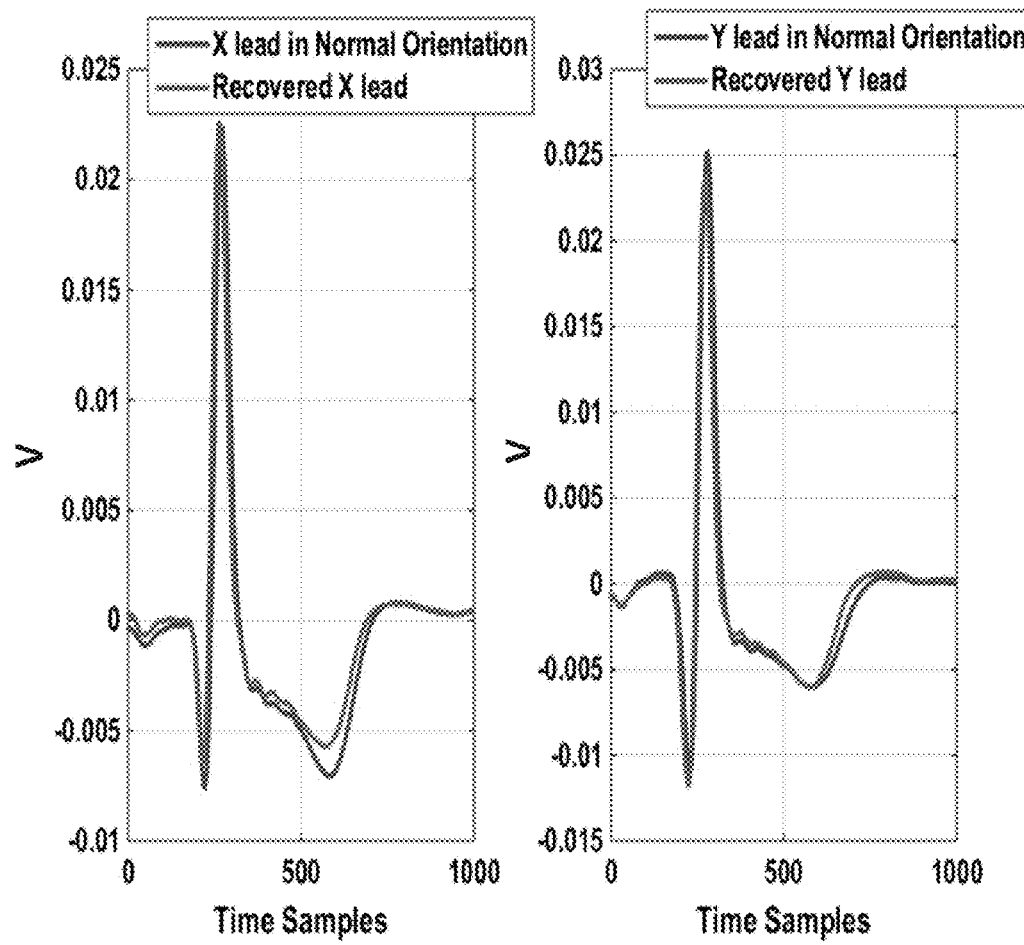
FIG. 17B shows the comparison of X and Y Leads recorded with normal electrode placement and software-recovered leads (electrodes were rotated in the clockwise direction), in accordance with an embodiment of the present invention.

FIG. 16A illustrates the projection of the cardiac vector in the XY plane for a normal orientated VCG device, the projection when the VCG device is rotated by 45° in the clockwise direction, and the software-corrected cardiac vector projection. FIG. 16B shows a similar figure, wherein the integrated VCG device was inadvertently rotated in the clockwise direction. FIG. 17A illustrates the X and Y leads when recorded in the normal orientation and when recovered from an VCG device rotated in a clockwise direction and FIG. 17B illustrates the X and Y leads when recorded in the normal orientation and when recovered from an VCG device rotated in and anti-clockwise direction. In an additional embodiment, the angle of rotation to correct the effects of inadvertent rotation of the device may be analytically computed as an alternative to the iterative approach.

It is further contemplated herein that the battery in the device can be designed to accommodate the long-life requirements that are important for implanted devices. Similarly, a low-power wireless protocol (e.g., BLUETOOTH Low Energy) can be chosen in order to adhere to the SAR (Specific Absorption Ratio) power limitation requirements in the body.

To save power, the device does not necessarily continuously wirelessly communicate, but may have embedded intelligence that determines and only communicates to report cardiac events. This enables event-driven communications, which is power conserving relative to continuous transmission.

Another optional feature is that the implanted VCG device wirelessly communicates, with or forms a network with other cardiac implanted devices within the patient (e.g., pacemaker, ICD, etc. ), or with other devices where the coordinated information recorded and transmitted by the network of devices is of medical benefit to the user, operator, medical team, etc. For example, the implanted VCG device can communicate advanced/intelligent actuation decisions to a pacemaker or train the pacemaker to make better decisions. It is expected that the limited sensing capability and intelligence present in the cardiac implant can benefit significantly from the VCG device's monitoring capability. As such, the number of false positive shocks administered by these cardiac implants, which is presently a problem, can be significantly reduced by the cardiac implant being trained to make better decisions.

Importantly, it has been shown herein that a VCG device can be made with all five electrodes (X+/−, Y+/− and Z+) leads fully integrated into the device, thereby eliminating any external leads or permitting only a single external electrode (Z−). The Z-axis lead can also make electrical contact with the skin or not make electrical contact with the skin, or be incorporated into a main external integrated device by adding depth between the two leads. Further, the devices may be calibrated relative to a 12-lead ECG. The VCG devices may also measure respiration via measured changes in bio-impedance, along with controlling or training cardiac implants, such as pacemakers.

The inventive integrated vectorcardiogram system of the present invention allows long term and continuous remote monitoring of a patient's electrical heart activity. The implications are potentially profound and include: (1) providing a less expensive, less obtrusive, device compared to the 12-lead ECG system (the "gold standard"); (2) comprehensive and continuous remote tele-monitoring of a patient; (3) capable of replacing the current Holter monitor system; (4) ICU cardiac monitoring becoming much less complex and costly; (5) physicians potentially sending patients home earlier because the doctors can have continuous remote monitoring of the patients; (6) Cardiac Implants benefitting from intelligent monitoring information; and (7) predicting potentially fatal cardiac events and alerting patients to seek medical care to avert said event The primary component of the Integrated Vectorcardiogram system of the present invention is the integrated VCG device. Presented herein are proof-of-concept experimental results that strongly support the above assertions. Moreover, it is shown herein how to collect and process the signals of the electrical activity of the heart using the integrated VCG device. The learning system and communication capabilities are part of the integrated VCG system, such that it can learn the patterns of the collected data and make decisions that are sent to the pacemaker (ICD/CRT) that control actuation. As such, the VCG learning system of the present invention may also be trained to not only recognize, but predict cardiac abnormalities.

The vectorcardiogram system of the present invention captures the electrical condition of the heart by recording the 3-D cardiac vector signal, using a minimal lead distance. The captured signals are then filtered and converted to digital data. The data is then processed using an algorithm for noise removal and re-orthogonalization. The corrected VCG leads are then either transmitted to the hospital/physician/implanted device, as-is or after conversion to a 12-lead ECG.

The present invention may be embodied on various computing platforms that perform actions responsive to software-based instructions. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM ), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++ or the like and conventional procedural programming languages, such as the "C" programming language or similar programming languages.

Aspects of the present invention are described below with reference to illustrations and/or block diagrams of methods, apparatus (systems) and computer program products according to embodiments of the invention. It will be understood that each element in the illustrations can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A vectorcardiogram device for measuring cardiac electrical activity of a patient, the device comprising:
   a pair of substantially orthogonal X-axis electrodes and a pair of substantially orthogonal Y-axis electrodes, the electrodes contained within a housing adapted to be in contact with a patient in a vectorcardiogram measurement position to sense cardiac electrical signals of the patient;
   analog processing circuitry contained within the housing, the analog processing circuitry coupled to receive the cardiac electrical signals sensed by the pair of substantially orthogonal X-axis electrodes and the pair of substantially orthogonal Y-axis electrodes;
   an analog-to-digital converter contained within the housing, the analog-to-digital converter coupled to the analog processing circuitry to convert the cardiac electrical signals to digital vectorcardiogram data;
   a memory storing a reference cardiac vector, wherein the reference cardiac vector is based upon electrocardiogram (ECG) data and vectorcardiogram (VCG) data obtained during an initial placement of the vectorcardiogram device;
   a digital signal processor contained within the housing, the digital signal processor coupled to receive the digital vectorcardiogram data from the analog-to-digital converter and to correct the digital vectorcardiogram data for a misplacement of the vectorcardiogram device after the initial placement using the reference cardiac vector to generate processed digital vectorcardiogram data; and
   telemetry circuitry contained within the housing, the telemetry circuitry coupled to receive the processed digital vectorcardiogram data from the digital signal processor and to transmit the processed digital vectorcardiogram data to a remote device.

2. The vectorcardiogram device of claim 1, further comprising a first Z-axis electrode of a pair of substantially orthogonal Z-axis electrodes, the first Z-axis electrode contained within the housing adapted to be in contact with a patient in a vectorcardiogram measurement position and coupled to the analog processing circuitry, the first Z-axis electrode to sense cardiac electrical signals of the patient and the analog processing circuitry to receive the cardiac electrical signals from the first Z-axis electrode.

3. The vectorcardiogram device of claim 2, further comprising a second Z-axis electrode of the pair of substantially orthogonal Z-axis electrodes adapted to be in contact with the patient in a vectorcardiogram measurement position and coupled to the analog processing circuitry, the second Z-axis electrode to sense cardiac electrical signals of the patient and the analog processing circuitry to receive the cardiac electrical signals from the second Z-axis electrode.

4. The vectorcardiogram device of claim 3, wherein the second Z-axis electrode of the pair of substantially orthogonal Z-axis electrodes is contained within the housing.

5. The vectorcardiogram device of claim 3, wherein the first Z-axis electrode and the second Z-axis electrode of the pair of substantially orthogonal Z-axis electrodes are separated by a predetermined distance within the housing.

6. The vectorcardiogram device of claim 3, wherein the second Z-axis electrode of the pair of substantially orthogonal Z-axis electrodes is coupled to the analog processing circuitry by an external lead and is adapted to contact the patient in a measurement position.

7. The vectorcardiogram device of claim 1, wherein the analog processing circuitry comprises at least one amplifier.

8. The vectorcardiogram device of claim 7, wherein the analog processing circuitry comprises at least one filter coupled to the at least one amplifier.

9. The vectorcardiogram device of claim 8, wherein the analog processing circuitry comprises at least one amplifier buffer coupled between the at least one filter and the analog-to-digital converter.

10. The vectorcardiogram device of claim 1, further comprising a microcontroller coupled to the analog processing circuitry, the analog to digital converter, the digital signal processor and the telemetry circuitry.

11. The vectorcardiogram device of claim 10, further comprising at least one of a user interface and a display coupled to the microcontroller.

12. The vectorcardiogram device of claim 1, wherein the digital signal processor further comprises a transformation matrix to transform the digital vectorcardiogram (VCG) data to electrocardiogram (ECG) data.

13. The vectorcardiogram device of claim 1, wherein the reference cardiac vector is further based upon:
   transforming the ECG data measured during the initial placement of the vectorcardiogram device to a normal VCG signal by a 3×12 inverse transformation matrix;
   comparing the normal VCG signal to the VCG data obtained during the initial placement of the vectorcardiogram device; and
   determining a quantity for rotating the digital vectorcardiogram data that minimizes an error between the normal VCG signal and the VCG data obtained during the initial placement of the vectorcardiogram device.

14. The vectorcardiogram device of claim 13, wherein the 3×12 inverse transformation matrix is patient specific.

15. The vectorcardiogram device of claim 1, wherein the telemetry circuitry is wireless telemetry circuitry.

16. The vectorcardiogram device of claim 1, wherein the remote device is selected from the group consisting of a computer, a smartphone, a native device, a tablet, a server, or other electronic device.

17. A method for measuring cardiac electrical activity of a patient, the method comprising:
   positioning a vectorcardiogram device in an initial measurement position relative to a patient, wherein the vectorcardiogram device comprises;
      a pair of substantially orthogonal X-axis electrodes and a pair of substantially orthogonal Y-axis electrodes, the electrodes contained within a housing adapted to be in contact with a patient in a measurement position to sense cardiac electrical signals of the patient;
      analog processing circuitry contained within the housing, the analog processing circuitry coupled to receive the cardiac electrical signals sensed by the pair of substantially orthogonal X-axis electrodes and the pair of substantially orthogonal Y-axis electrodes;
      an analog-to-digital converter contained within the housing, the analog-to digital converter coupled to the analog processing circuitry to convert the cardiac electrical signals to digital vectorcardiogram data;
      a digital signal processor contained within the housing, the digital signal processor coupled to receive the digital vectorcardiogram data from the analog-to-digital converter to generate processed digital vectorcardiogram data:
      telemetry circuitry contained within the housing, the telemetry circuitry coupled to the receive the processed digital vectorcardiogram data from the digital signal processor and to transmit the data to a remote device;
   obtaining electrocardiogram (ECG) data and vectorcardiogram (VCG) data using the vectorcardiogram device positioned at the initial measurement position;
   generating a reference cardiac vector from the ECG data and VCG data obtained at the initial measurement position;
   storing the reference cardiac vector in a memory at the vectorcardiogram device;
   correcting, at the digital signal processor and using the reference cardiac vector, the digital vectorcardiogram data for a misplacement of the vectorcardiogram device after the initial placement of the vectorcardiogram device to generate the processed digital vectorcardiogram data; and
   transmitting the processed digital vectorcardiogram data to a remote device.

18. The method of claim 17, wherein the vectorcardiogram device further comprises a first Z-axis electrode of a pair of substantially orthogonal Z-axis electrodes, the first Z-axis electrode contained within the housing adapted to be in contact with a patient in a vectorcardiogram measurement position and coupled to the analog processing circuitry, the first Z-axis electrode to sense cardiac electrical signals of the patient and the analog processing circuitry to receive the cardiac electrical signals from the first Z-axis electrode.

19. The method of claim 18, wherein the vectorcardiogram further comprises a second Z-axis electrode of the pair of substantially orthogonal Z-axis electrodes adapted to be in contact with the patient in a vectorcardiogram measurement position and coupled to the analog processing circuitry, the second Z-axis electrode to sense cardiac electrical signals of the patient and the analog processing circuitry to receive the cardiac electrical signals from the second Z-axis electrode.

20. The method of claim 19, wherein the second Z-axis electrode of the pair of substantially orthogonal Z-axis electrodes is contained within the housing.

21. The method of claim 19, wherein the second Z-axis electrode of the pair of substantially orthogonal Z-axis electrodes is coupled to the analog processing circuitry by an external lead and is adapted to contact the patient in a measurement position.

22. The method of claim 17, wherein the measurement position is external to the patient.

23. The method of claim 17, wherein the measurement position in internal to the patient.

24. The method of claim 17, further comprising transforming the digital vectorcardiogram (VCG) data to electrocardiogram (ECG) data using a transformation matrix.

25. The method of claim 17, wherein generating the reference cardiac vector from the ECG data and VCG data obtained at the initial measurement position further further comprises:
   transforming the ECG data measured during the initial placement of the vectorcardiogram device to a normal VCG signal by a 3×12 inverse transformation matrix;
   comparing the normal VCG signal to the VCG data obtained at the initial measurement position of the vectorcardiogram device; and
   determining a quantity for rotating the digital vectorcardiogram data that minimizes an error between the normal VCG signal and the VCG data obtained at the initial measurement position of the vectorcardiogram device.

26. The method of claim 18, wherein the 3×12 inverse transformation matrix is patient specific.

27. A system for measuring the cardiac electrical activity of a patient, the system comprising:
   a vectorcardiogram device for measuring cardiac electrical activity of a patient, the device comprising:
      a pair of substantially orthogonal X-axis electrodes, a pair of substantially orthogonal Y-axis electrodes and a first Z-axis electrode of a pair of substantially orthogonal Z-axis electrodes, the electrodes contained within a housing adapted to be in contact with a patient in a vectorcardiogram measurement position to sense cardiac electrical signals of the patient;
      analog processing circuitry contained within the housing, the analog processing circuitry coupled to receive the cardiac electrical signals sensed by the pair of substantially orthogonal X-axis electrodes, the pair of substantially orthogonal Y-axis electrodes and the first Z-axis electrode of the pair of substantially orthogonal Z-axis electrodes;
a second Z-axis electrode of the pair of substantially orthogonal Z-axis electrodes adapted to be in contact with the patient in a vectorcardiogram measurement position and coupled to the analog processing circuitry, the second Z-axis electrode to sense cardiac electrical signals of the patient and the analog processing circuitry to receive the cardiac electrical signals from the second Z-axis electrode;
an analog-to-digital converter contained within the housing, the analog-to-digital converter coupled to the analog processing circuitry to convert the cardiac electrical signals to digital vectorcardiogram data;
a memory storing a reference cardiac vector, wherein the reference cardiac vector is based upon electrocardiogram (ECG) data and vectorcardiogram (VCG) data obtained during an initial placement of the vectorcardiogram device;
a digital signal processor contained within the housing, the digital signal processor coupled to receive the digital vectorcardiogram data from the analog-to-digital converter and to correct the digital vectorcardiogram data for a misplacement of the vectorcardiogram device after the initial placement, using the reference cardiac vector, to generate processed digital vectorcardiogram data;
telemetry circuitry contained within the housing, the telemetry circuitry coupled to receive the processed digital vectorcardiogram data from the digital signal processor;
a remote device in communication with the telemetry circuitry of the vectorcardiogram device; and
a cardiac resynchronization therapy (CRT) pacemaker in communication with the telemetry circuitry of the vectorcardiogram device.

* * * * *

UNITED STATES PATENT AND TRADEMARK OFFICE
CERTIFICATE OF CORRECTION

PATENT NO. : 9,451,890 B2  
APPLICATION NO. : 14/801514  
DATED : September 27, 2016  
INVENTOR(S) : Richard Dennis Gitlin et al.

Page 1 of 1

It is certified that error appears in the above-identified patent and that said Letters Patent is hereby corrected as shown below:

On the Title Page

Item (72) Inventors should read:

(72) Inventors: Richard Dennis Gitlin, Tampa, FL (US); Gabriel Eduardo Arrobo, Emeryville, CA (US); Peter Jeffrey Fabri, Tampa, FL (US); Thomas Peter Ketterl, Tampa, FL (US); Calvin Perumalla, Tampa, FL (US)

Signed and Sealed this
Tenth Day of January, 2017

Michelle K. Lee
*Director of the United States Patent and Trademark Office*